(12) United States Patent
Sano et al.

(10) Patent No.: US 7,657,996 B2
(45) Date of Patent: Feb. 9, 2010

(54) TUBE CONNECTING APPARATUS AND TUBE CONNECTING METHOD

(75) Inventors: Hiroaki Sano, Nakakoma-gun (JP); Masaru Nagashimada, Nakakoma-gun (JP); Shinji Ishida, Isehara (JP); Satoshi Yamanushi, Nirasaki (JP); Hideya Fujihara, Nirasaki (JP); Osamu Sumiya, Kofu (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 736 days.

(21) Appl. No.: 10/525,972

(22) PCT Filed: Aug. 29, 2003

(86) PCT No.: PCT/JP03/11043

§ 371 (c)(1),
(2), (4) Date: Feb. 28, 2005

(87) PCT Pub. No.: WO2004/020179

PCT Pub. Date: Mar. 11, 2004

(65) Prior Publication Data

US 2006/0005371 A1    Jan. 12, 2006

(30) Foreign Application Priority Data

Aug. 30, 2002  (JP)  ............................ 2002-252315
Dec. 6, 2002   (JP)  ............................ 2002-356073

(51) Int. Cl.
*B23P 21/00*  (2006.01)
*B32B 37/00*  (2006.01)

(52) U.S. Cl. ........................................ 29/711; 156/296

(58) Field of Classification Search .................. 29/711, 29/468, 463, 33 T, 282; 156/296, 304.1, 156/304.2, 304.6, 538, 539, 556
See application file for complete search history.

(56) References Cited

FOREIGN PATENT DOCUMENTS

EP         0 044 204        1/1982

(Continued)

OTHER PUBLICATIONS

*Office Action issued Apr. 22, 2008 in corresponding Japanese Application No. 2002-252315 and English language translation.

(Continued)

*Primary Examiner*—John C Hong
(74) *Attorney, Agent, or Firm*—Buchanan Ingersoll & Rooney PC

(57) ABSTRACT

A tube connecting apparatus capable of stably and reliably connecting tubes in which liquid is contained and sealed is provided. A tube connecting apparatus 1 equips a first tube-holding assembly 2 and a second tube-holding assembly 3, each holding tube 8, 9 in which blood is contained and sealed in a parallel state. A first clamp 6 and a second clamp 7, each pressing the tubes to a flat state, is provided at the first tube-holding assembly 2 and the second tube-holding assembly 3. A tube-pushing member 10 which presses the tubes to a flat state is disposed movably to and integrally with the first clamp 6 at a side of the second clamp 7. The tube connecting apparatus 1 has a cutting mechanism 4, disposed between the first clamp 6 and the second clamp 7, for melting and cutting the tubes, and has a movement mechanism which moves the first tube-holding assembly 2 and the second tube-holding assembly 3 such that end portions to be connected contact closely each other.

20 Claims, 29 Drawing Sheets

FOREIGN PATENT DOCUMENTS

| | | |
|---|---|---|
| EP | 0 507 321 A1 | 10/1992 |
| EP | 0 515 811 A2 | 12/1992 |
| EP | 0 778 123 A2 | 6/1997 |
| JP | 61-30582 | 7/1986 |
| JP | 4-308731 | 10/1992 |
| JP | 6-91010 | 4/1994 |
| JP | 6-91010 A | 4/1994 |
| JP | 4073291182 * | 12/1995 |
| JP | 9-154920 | 6/1997 |
| WO | WO 02/066098 A1 | 8/2002 |

OTHER PUBLICATIONS

*Office Action issued Aug. 12, 2008 in corresponding Japanese Application No. 2002-252315 and English language translation.

* cited by examiner

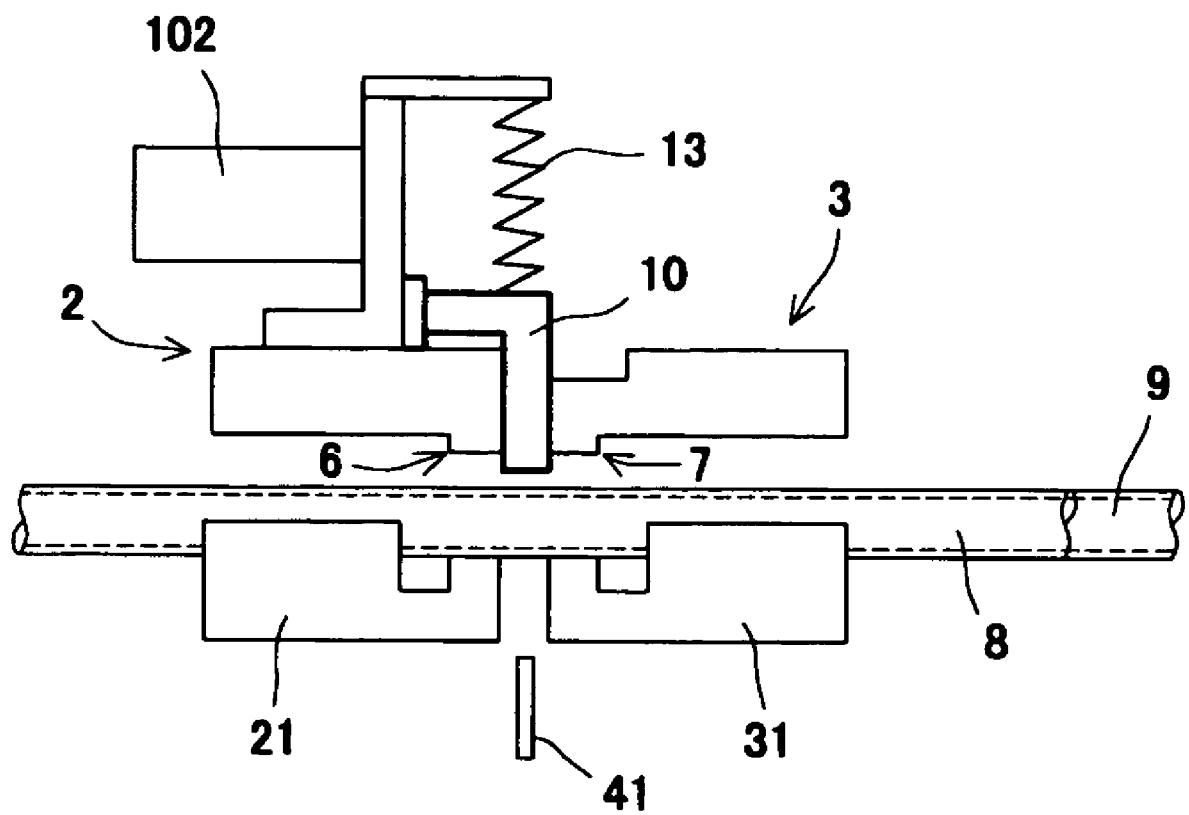

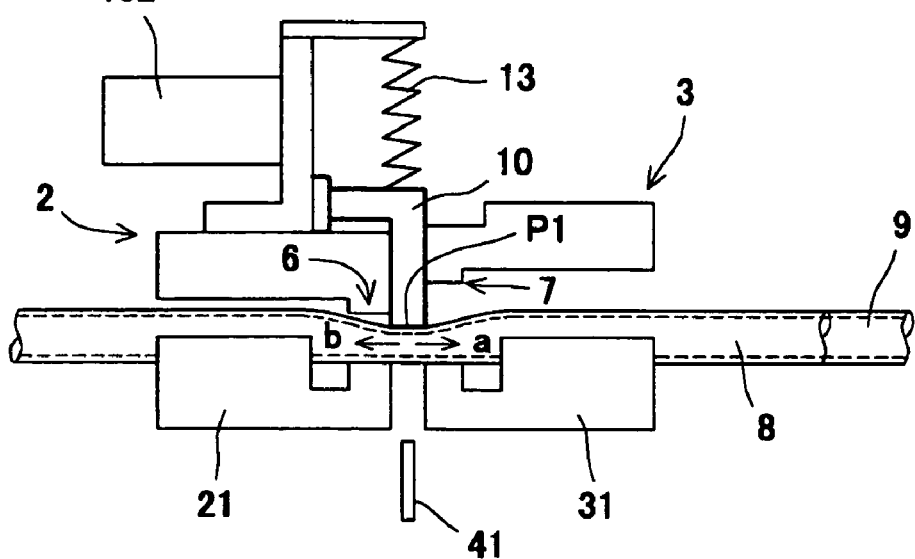
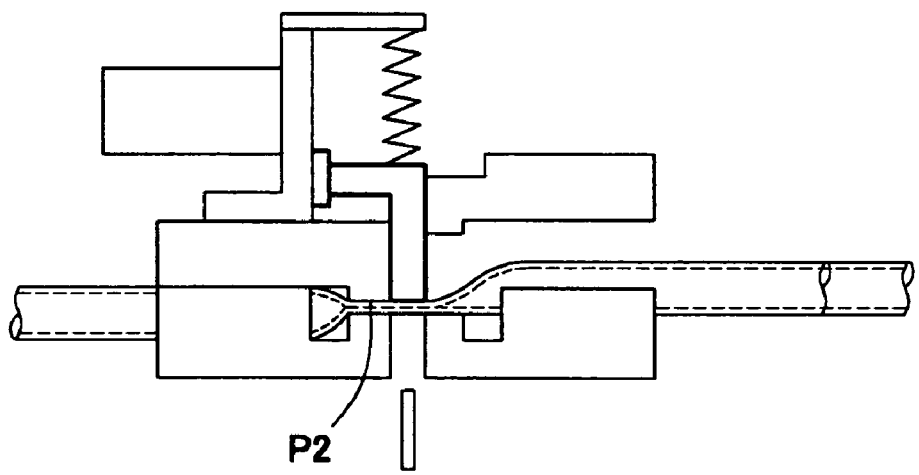
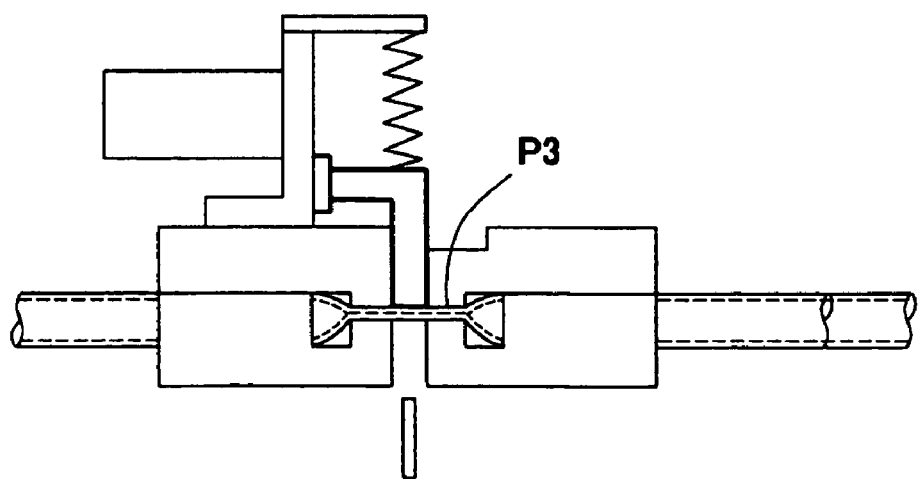

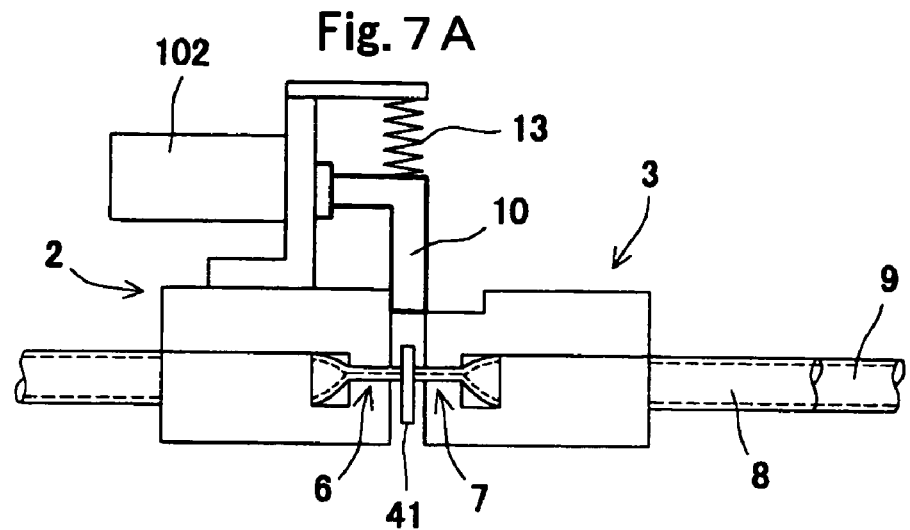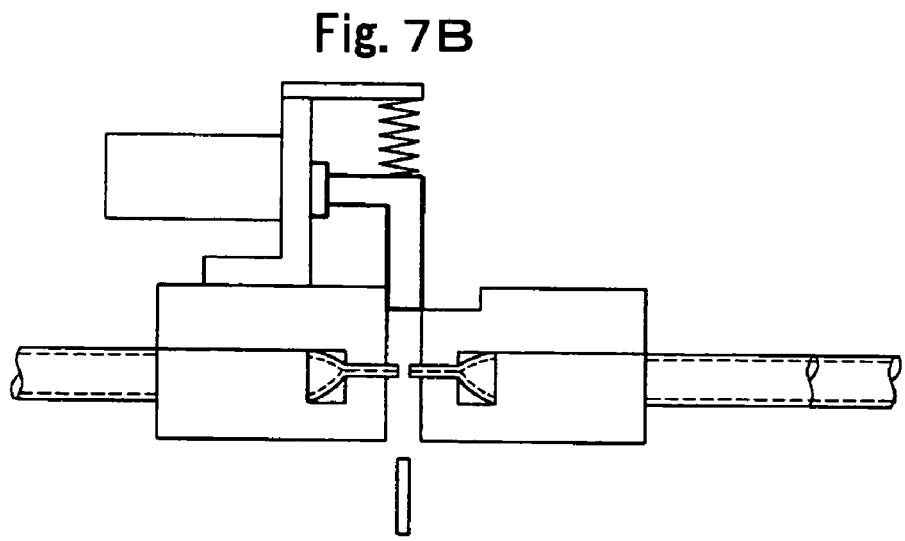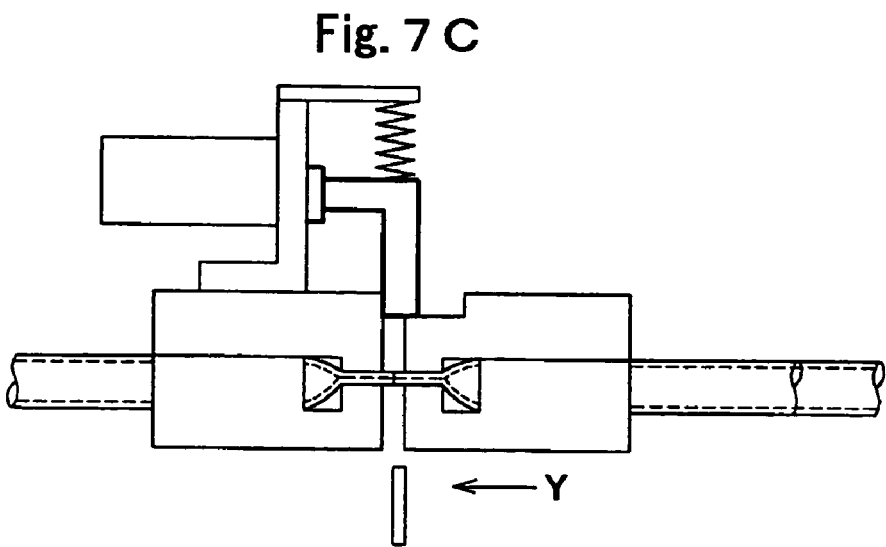

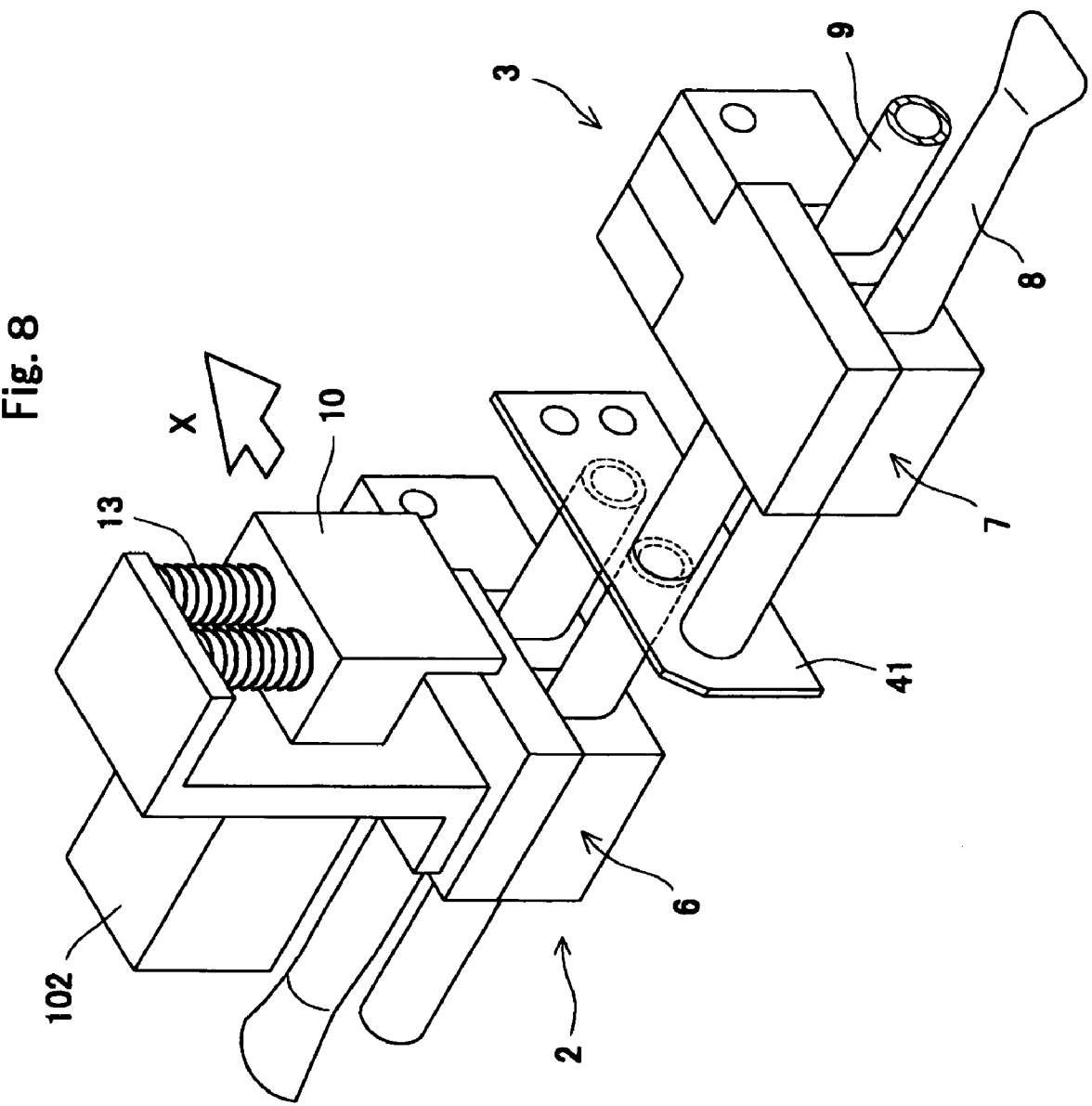

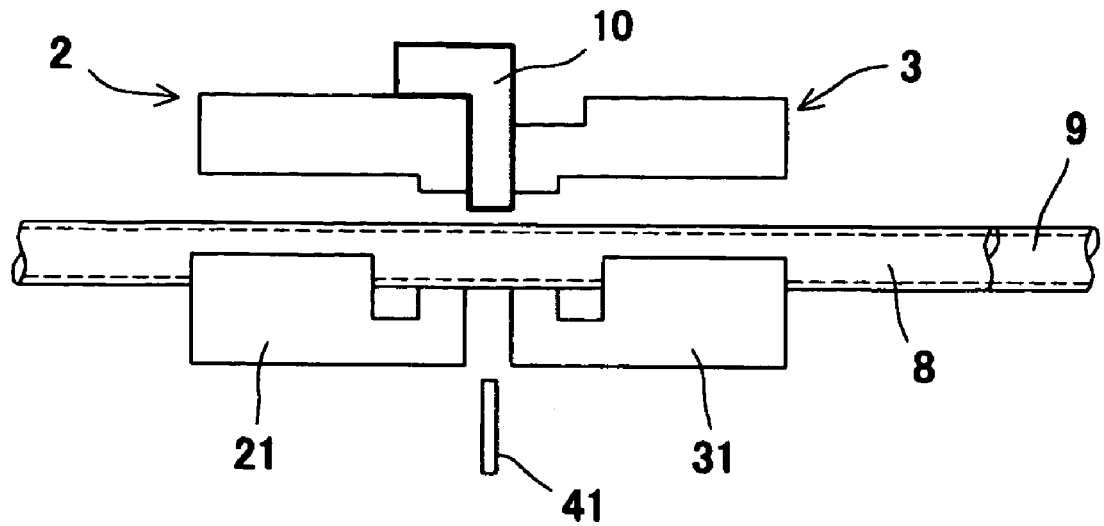
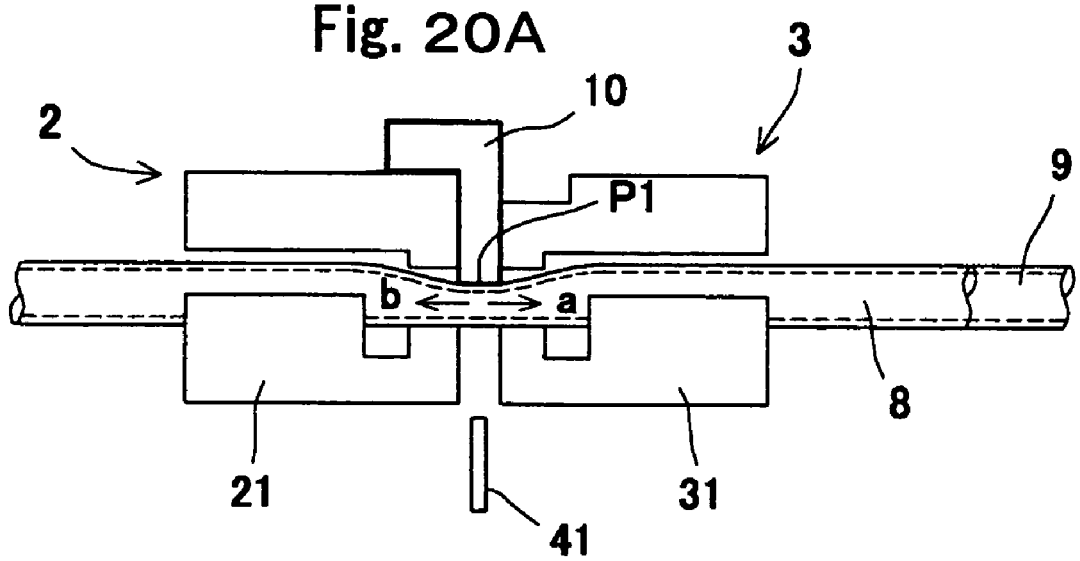
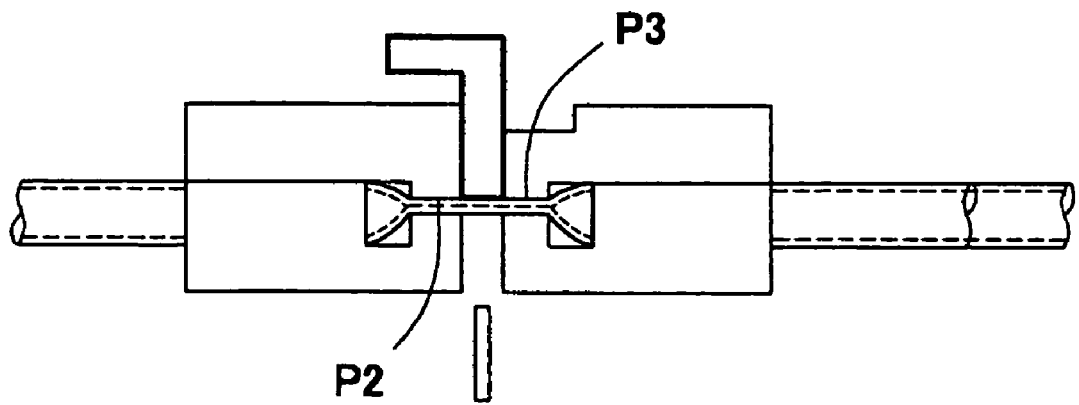

TUBE CONNECTING APPARATUS AND TUBE CONNECTING METHOD

RELATED APPLICATION DATA

This application claims the benefit of and priority to Patent Application No. 2002-252315, filed with the Japanese Patent Office (JPO) on Aug. 30, 2002 (30 Aug. 2), entitled "Tube Connecting Apparatus and Tube Connecting Method" and Patent Application No. 2002-356073, filed with the JPO on Dec. 6, 2002 (6 Dec. 2), entitled "Tube Connecting Apparatus".

BACKGROUND OF THE INVENTION

1. Field of the Invention

The present invention relates to a tube connecting apparatus and a tube connecting method that cuts and then connects flexible tubes, and in particular relates to a tube connecting apparatus and a tube connecting method that melts at least two flexible tubes by heat and then connects the tubes under a sterilized condition.

2. Description of Related Art

Conventionally, in a case that tube connecting between a blood-collecting bag and a blood-component bag in a blood transfusion system, exchanging between a dialytic-fluid bag and a waste-fluid bag in continuous ambulatory peritoneal dialysis (CAPD) or the like is carried out, it is necessary to connect tubes under a sterilized condition. An example of such an apparatus for connecting tubes under a sterilized condition is disclosed in JPB 61-30582. This tube connecting apparatus is equipped with a pair of holders (blocks) capable of holding two tubes to be connected in parallel and a cutting plate (plate-shaped heater element) capable of moving across the tubes which are placed between both of the holders. According to this tube connecting apparatus, the cutting plate is heated and moved to melt and cut the tubes in a state that the two tubes are held in parallel and in an opposite direction in grooves which are formed at the holders, then one of the holders is moved in a diameter direction (row direction) of the tubes to coincide cut ends of the tubes to be connected each other, and the cutting plate is extracted by moving it to an evacuated position to fuse (melt and connect) both of the tubes.

Further, a tube connecting apparatus which employs the same tube connecting method as the above apparatus and which has a first clamp and a second clamp which hold two tubes in a parallel state in order to improve reliability of tube connecting is disclosed in JPA 6-91010. The tube connecting apparatus has a first clamp movement mechanism that moves the first clamp in parallel to the second clamp, namely, that carries out merely forward or backward movement for advancing or retracting the first clamp, and a second clamp movement mechanism that moves the second clamp merely in a direction that the second clamp approaches/separates to/from the first clamp.

Furthermore, an apparatus, which employs the same principle of heating, melting and then connecting the tubes each other under a sterilized condition by utilizing a cutting plate, yet which connects the tubes in a state that liquid in the tubes is kept contained without leaking the liquid even in a case that the liquid remains inside the tubes before the tubes are cut, is also disclosed. For example, JPA 4-308731 discloses a technique that two tubes (a first tube, a second tube) are held on the same rotation locus respectively according to a pair of tube holders allowed to rotate relatively, after the two tubes are cut between the holders by a heated cutting plate, the tube holders are rotated such that a cut end face of one end side of the first tube aligns (corresponds to) a cut end face of another side of the second tube, and the cutting plate is evacuated to fuse both of the tubes.

Moreover, a tube connecting apparatus which is capable of not only connecting tubes in a state that liquid inside the tubes is kept contained and sealed without leaking the liquid but which can realize downsizing of the apparatus and of parts for the apparatus due to a small moving amount of the tubes at the time of connecting the tubes, is also disclosed. For example, JPA 9-154920 discloses a technique that two tubes to be connected are accommodated and held in two tube-holding assembly (a first tube-holding assembly, a second tube-holding assembly) in a contacted (piled) state with each other, after the two tubes are cut by a heated cutting plate, the second tube-holding assembly is rotated by 180 degrees relatively to the first tube-holding assembly such that cut end faces of the tubes are replaced with each other for alignment, and the cutting plate is evacuated to fuse both of the tubes.

However, in the conventional tube connecting apparatuses, even in any embodiment of the apparatuses in which the two tubes are arranged in parallel in a horizontal or vertical direction in a separated or contacted state, if liquid inside the tubes includes protein such as blood or the like, residual liquid inside the tubes between the two tube-holding assemblies (holders) remains at the end faces of the tubes to be connected when the tubes are cut by the cutting plate. For this reason, there is a problem in that connecting strength between the tubes is remarkably weakened. Namely, in the conventional apparatuses, in a case that liquid is contained and sealed in either one of the tubes, since the tube end face of one side thereof is moved in a state of contacting the cutting plate at the time of moving the tube-holding assembly so as to face the end portions of the tubes to be connected each other via the cutting plate and the residual liquid in the tubes is excluded or removed to some degree at this time, it is possible to connect the tubes each other although connecting strength thereof is lowered. However, it was difficult to connect two tubes each other stably in a case that both of the two tubes contain and seal liquid such as blood or the like.

SUMMARY OF THE INVENTION

In view of the above circumstances, an object of the present invention is to provide a tube connecting apparatus and a tube connecting method capable of connecting tubes in which liquid is contained and sealed each other stably and reliably.

In order to achieve the above object, a first aspect of the present invention is directed to a tube connecting apparatus having a first holding assembly and a second holding assembly which hold at least two flexible tubes approximately in a parallel state, comprising: a first pressing unit which is provided at the first holding assembly and which presses the tubes to a flat state; a second pressing unit which is provided at the second holding assembly and which presses the tubes to a flat state; a third pressing unit which is disposed between the first and second pressing units and which presses the tubes to a flat state; a cutting unit which cuts the tubes between the first and second pressing units; and a movement unit which moves at least one of the first and second holding assemblies to change relatively positions of the tubes cut by the cutting unit such that end portions to be connected contact closely each other.

In the first aspect, at least two flexible tubes held approximately in a parallel state by the first holding assembly and the second holding assembly are pressed by the third pressing unit to a flat state, and then, pressed to a flat state by the first and second pressing units. Even if liquid is contained and sealed in the two flexible tubes, because the third pressing unit is disposed between the first and second pressing units, the liquid inside the tubes is excluded from pressing positions in the order of the third pressing unit, the first pressing unit and the second pressing unit (or the third pressing unit, the second pressing unit and the first pressing unit). The tubes are cut between the first and second pressing units by the cutting unit, then, at least one of the first and second holding assemblies is driven to move by the movement unit to change relatively positions of the tubes cut by the cutting unit such that end portions to be connected contact closely each other, thereby the tubes are connected. According to the present aspect, since the tubes are pressed by the third pressing unit prior to being pressed by the first and second pressing units, even if liquid is contained and sealed in the tubes, residual liquid is excluded from pressing positions thereof. Accordingly, the tubes can be connected with each other without being influenced by the liquid which is contained and sealed in the tubes when the pressing positions of the tubes are cut by the cutting unit and the at least one of the first and second holding assemblies is moved to connect the tubes each other by the movement unit.

In the first aspect, the third pressing unit may be disposed movably to and integrally with either one of the first holding assembly and the second holding assembly. Further, the movement unit may be constituted to have a first movement unit which moves the first holding assembly in a first direction which is a width direction of the tubes and a second movement unit which moves the second holding assembly in a second direction which is a length direction of the tubes and which is a direction orthogonal to the first direction.

It is preferable that the third pressing unit has an energizing section which energizes the tubes to a pressing position at which the tubes are pressed to a flat state and a stopping section which regulates energizing force of the energizing section to stop movement of the third pressing unit. In the embodiment, the stopping section may have a first stopping member for stopping movement of the third pressing unit in a direction of pushing the tubes further from the pressing position and a second stopping member for stopping movement of the third pressing unit to locate the third pressing unit at an evacuating position which is separated from the pressing position so as to allow the cutting unit to cut the tubes. Such a first stopping member may comprise a stepped portion which engages the third pressing unit and which is formed at a part of either one of the first and second pressing units which is disposed adjacent to the third pressing unit, and the second stopping member may have a lever member for moving the third pressing unit so as to engage and hold the third pressing unit at the evacuating position and an actuator for actuating the lever member movably. Further, the cutting unit may have a cutting plate for melting and cutting the tubes in a heated state, a cutting-plate holding section for holding the cutting plate and a cutting-plate movement section for moving the cutting-plate holding section, and, when the cutting-plate holding section is moved by the cutting-plate movement section, the third pressing unit is moved to the evacuating position while resisting the energizing force of the energizing section in a state that a first projection member formed at a part of the cutting-plate holding section engages a second projection member formed at a part of the third pressing unit.

Further, in a case that the tube connecting apparatus further comprises an evacuation unit which evacuates the third pressing unit to an evacuating position which is separated from a pressing position at which the tubes are pressed to a flat state, and the cutting unit cuts the tubes between the first and second pressing units in a state that the third pressing unit is evacuated to the evacuating position by the evacuation unit, the tubes which are pressed to a flat state by the first and second pressing units and which are in a state that residual liquid is excluded from the pressing positions can be cut smoothly without causing interference between the third pressing unit and the cutting unit. In this embodiment, it is preferable that the movement unit has a first movement unit which moves the first holding assembly in a first direction which is a width direction of the tubes and a second movement unit which moves the second holding assembly in a second direction which is a length direction of the tubes and which is a direction orthogonal to the first direction, the first movement unit moves the first holding assembly in the first direction to change relatively positions of the tubes cut by the cutting unit such that end portions of the tubes to be connected face each other, the second movement unit moves the second holding assembly in the second direction such that the end portions of the tubes to be connected contact closely each other, and a distance between the first pressing unit provided at the first holding assembly which is movable in the first direction and the cutting unit is set to be larger than a distance between the second pressing unit provided at the second holding assembly which is movable in the second direction and the cutting unit, and it is more preferable that a moving distance of the first holding assembly in the first direction is set to be larger than a moving distance of the second holding assembly in the second direction.

Furthermore, in the first aspect, an embodiment can be employed that the first pressing unit has a first pressing section for pressing the tubes to a flat state and a first supporting section for supporting the tubes which are pressed by the first pressing section, the second pressing unit has a second pressing section for pressing the tubes to a flat state and a second supporting section for supporting the tubes which are pressed by the second pressing section, and further comprising: an evacuation guiding unit which guides the third pressing unit in a direction of an evacuating position when the cutting unit cuts the tubes; and a stopping unit which is provided at the first or second pressing unit and which stops the third pressing unit to locate the third pressing unit at the evacuating position.

In such an embodiment, since the third pressing unit is guided in a direction of an evacuating position by the evacuation guiding unit and is located to stop at the evacuating position by the stopping unit which is disposed at the first or second pressing unit, then the tubes are cut between the first and second pressing units by the cutting unit, stability on cutting and connecting operation to the tubes can be improved more. In this embodiment, it is preferable that the tube connecting apparatus further comprises an energizing unit which is disposed adjacent to the stopping unit and which energizes the stopping unit in a direction of the third pressing unit. A groove portion may be formed at a part of the third pressing unit, and when the third pressing unit is guided to the evacuating position by the evacuation guiding unit, the stopping unit may engage the groove portion to stop the third pressing unit at the evacuating position. Further, the cutting unit may have a cutting plate for melting and cutting the tubes in a heated state, a cutting-plate holding section for holding the cutting plate and a cutting-plate movement section for moving the cutting-plate holding section, and the evacuation guiding unit may be connected or integrally formed with the cutting-plate holding section. Further, when the tube connecting apparatus further comprises a cancellation unit which is provided at the first or second supporting unit and which cancels a stopping state of the third pressing unit according to the stopping unit, work efficiency can be improved since a time for resetting to an initial state by canceling an engaging state is shortened. In this case, the cancellation unit may cancel the stopping state of the third pressing unit according to the stopping unit linking with separating movement of the first or second pressing unit from a side of the first or second supporting unit. At this time, the stopping unit may have an inclined face at a part thereof and the cancellation unit may have a rotatable roller member, and the stopping state of the third pressing unit may be canceled in a manner that the stopping unit leaves the groove portion of the third pressing unit due to that the stopping unit is pushed along the inclined face by the roller member. It is preferable that one of the first or second pressing unit has a projection portion projecting toward another of the first or second pressing unit and the another of the first or second pressing unit has a groove portion or a dented portion into which the projection portion is inserted, and the groove portion or the dented portion has a shape which allows the projection portion to move when the first or second holding assembly is moved by the movement unit.

Further, in order to achieve the above object, a second aspect of the present invention is directed to a tube connecting method for cutting and then connecting at least two flexible tubes, comprising the steps of: pressing the tubes put approximately in a parallel state at a first position to deform the tubes to a flat state; pressing the tubes at a second position adjacent to the first position to hold the tubes in a flat state; pressing the tubes at a third position which is adjacent to the first position and which is a position opposing to the second position via the first position to hold the tubes in a flat state; advancing a heated cutting plate between the second and third positions to cut the tubes; moving relatively the tubes which have been cut to face end portions of the tubes to be connected each other; and evacuating the cutting plate from a predetermined cutting position located between the second and third positions to contact the end portions of the tubes closely each other for connecting the tubes.

In the second aspect, in the step of cutting the tubes, the cutting plate may advance to the cutting position linking with cancellation of pressing to the tubes at the first position, and when the tubes which have been cut are moved relatively, the tubes may be moved along at least one face side of the cutting plate in a state that the cutting plate is kept located at the cutting position.

With reference to embodiments below, materialized structure, operation, effect, scope to which the present invention is applicable and the like will become more apparent.

BRIEF DESCRIPTION OF THE DRAWINGS

With reference to the following drawings, embodiments of a tube connecting apparatus that cuts and then connects two tubes in which blood is contained and sealed and that the present invention is applied to will be explained.

FIG. 5 is an explanatory drawing showing operation 1 of the main portions of the tube connecting apparatus in tube connecting process and a front view illustratively showing a state that covering bodies of a first tube-holding assembly and a second tube-holding assembly begin to be closed;

FIG. 6 is a front view illustratively showing operations for the main portions of the tube connecting apparatus in the tube connecting process, FIG. 6A showing operation 2 thereof, FIG. 6B showing operation 3 thereof and FIG. 6C showing operation 4 thereof;

FIG. 7 is a front view illustratively showing operations for the main portions of the tube connecting apparatus in the tube connecting process, FIG. 7A showing operation 5 thereof, FIG. 7B showing operation 6 thereof and FIG. 6C showing operation 7 thereof;

FIG. 8 is a perspective view showing operation of the main portions of the tube connecting apparatus in the tube connecting process;

FIG. 19 is an explanatory drawing showing operation 1 of main portions of the tube connecting apparatus in the second embodiment and a front view illustratively showing a state that covering bodies of the first clamp and the second clamp begin to be closed;

FIG. 20 is a front view illustratively showing operations for the main portions of the tube connecting apparatus, FIG. 20A showing operation 2 thereof and FIG. 20B showing operation 3 thereof;

Figure 22A:
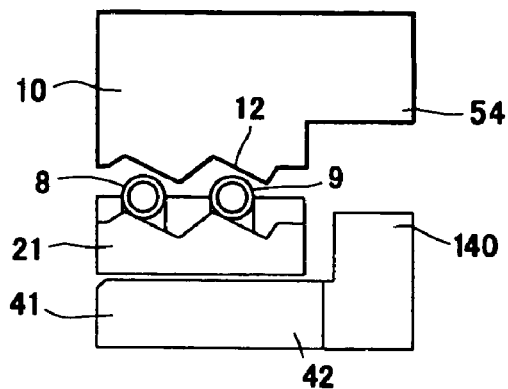
Figure 22B:
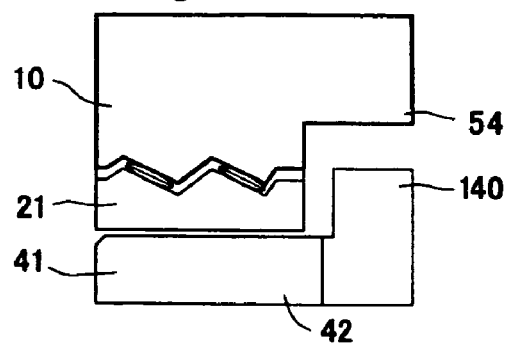
Figure 22C:
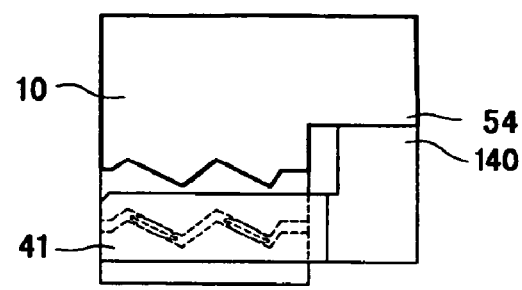
Figure 23:
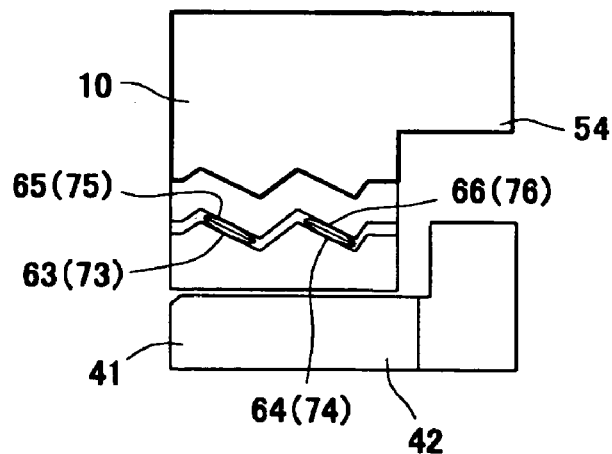
Figure 24:
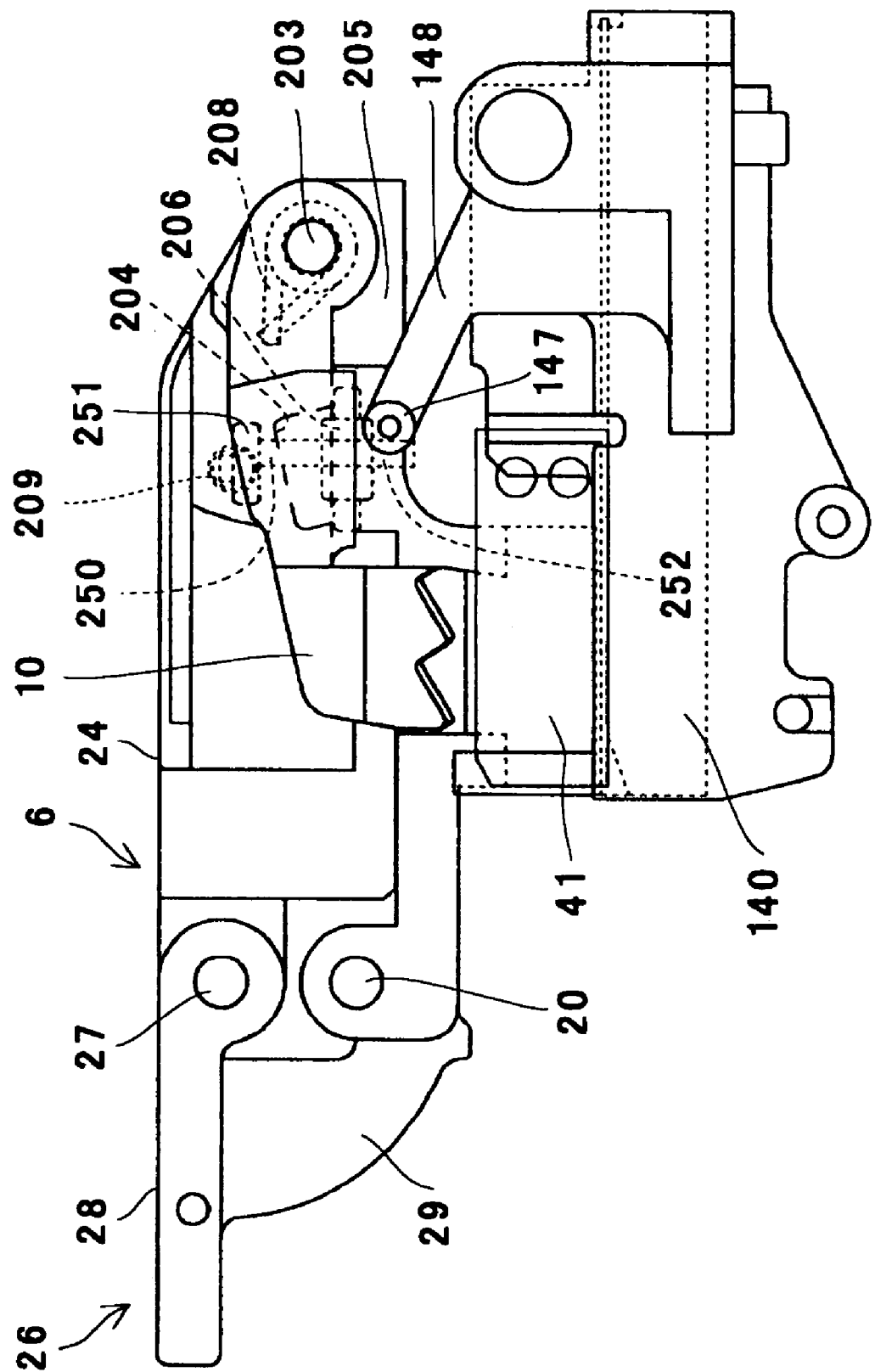
Figure 25:
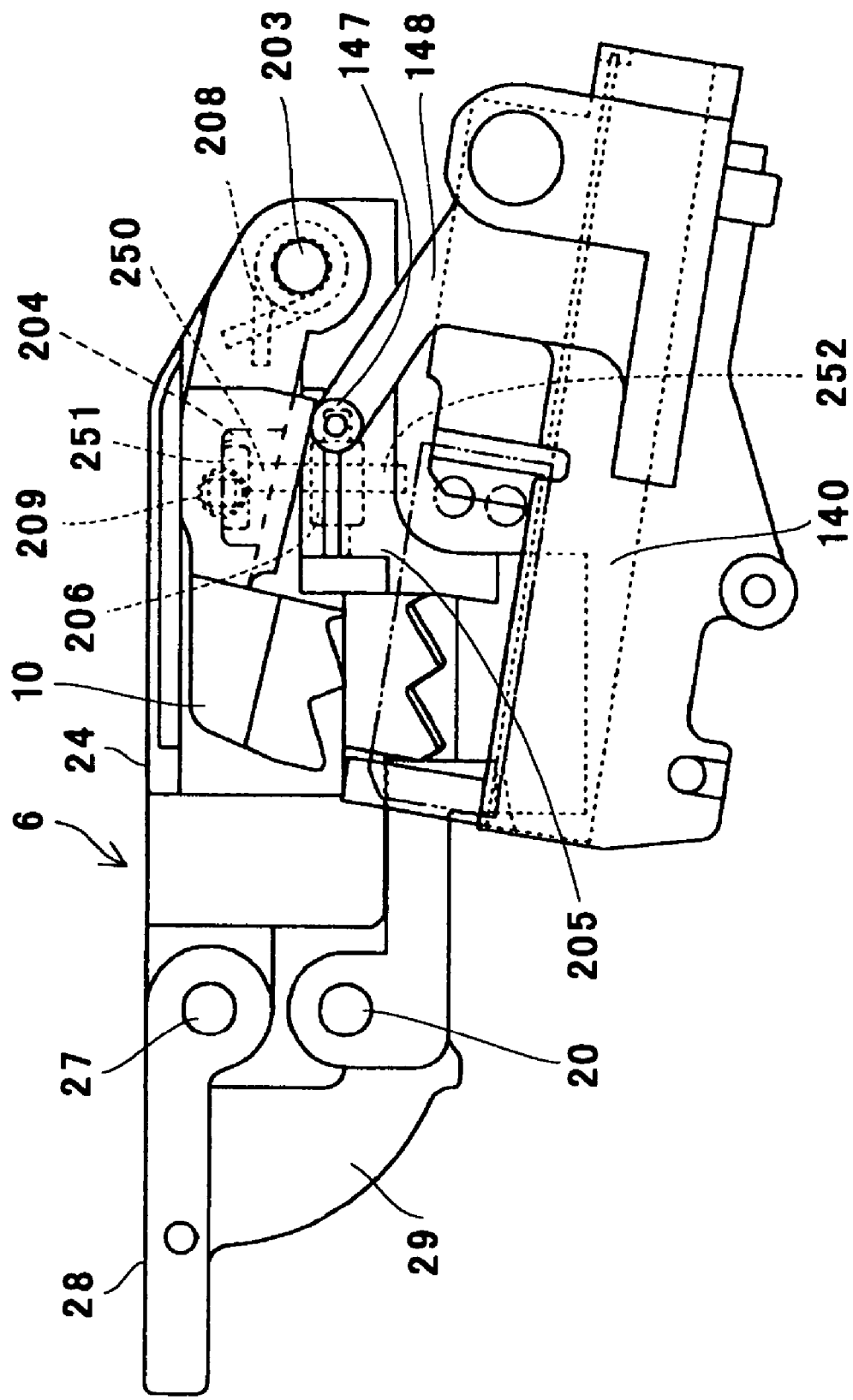
Figure 26A:
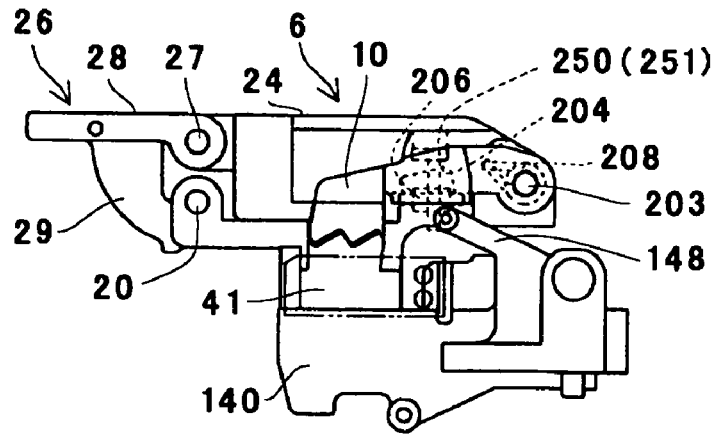
Figure 26B:
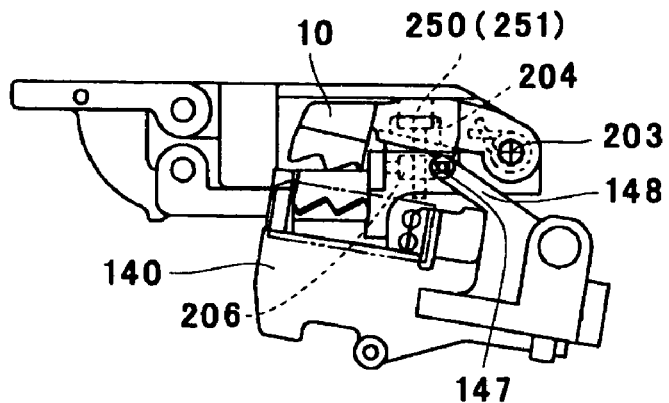
Figure 26C:
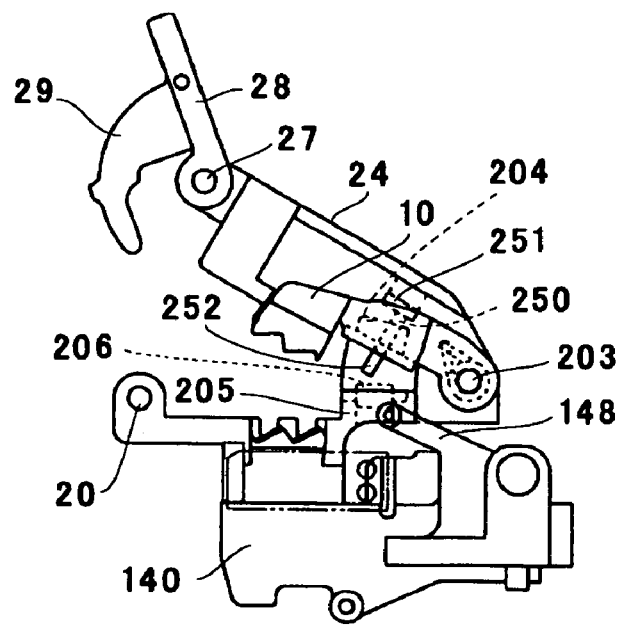
Figure 27A:
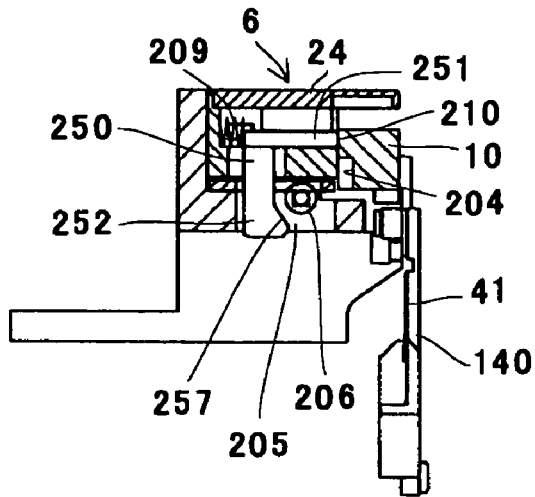
Figure 27B:
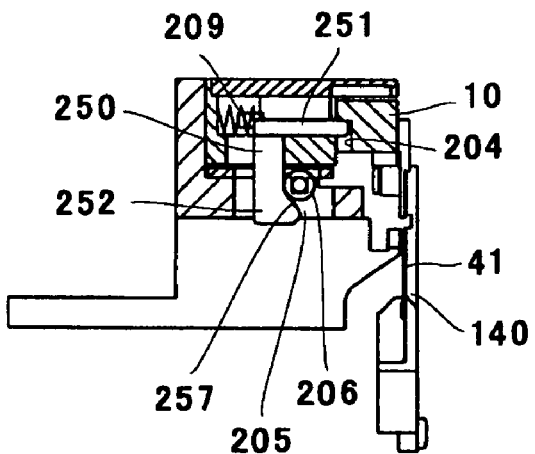
Figure 27C:
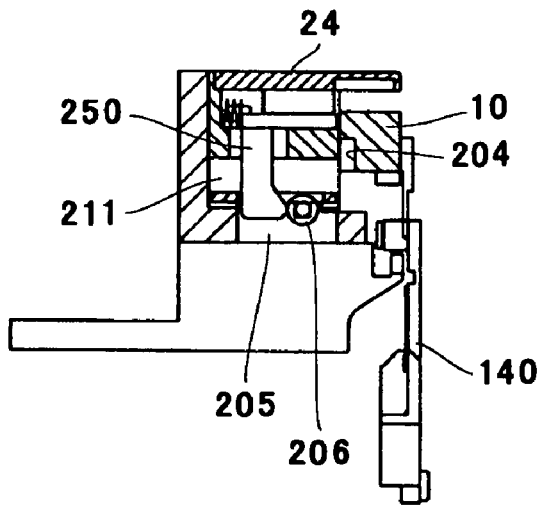
Figure 28:
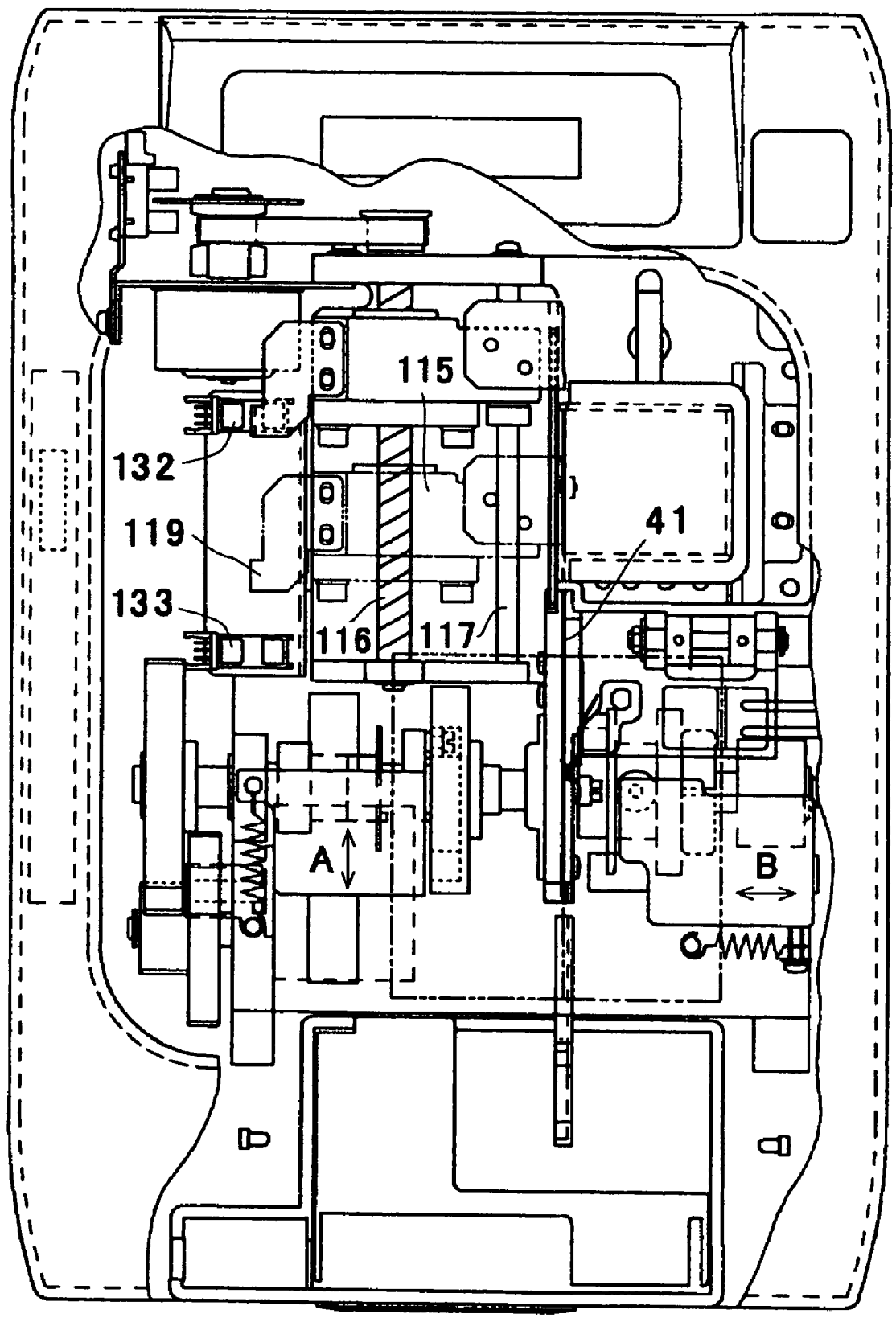
Figure 29A:
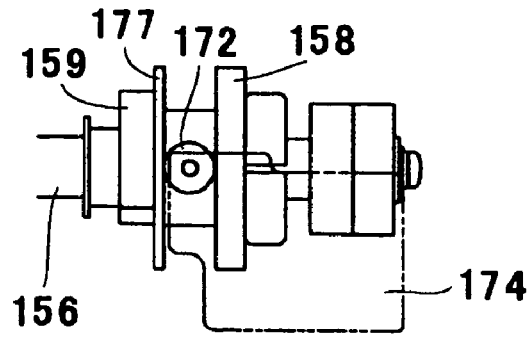
Figure 29B:
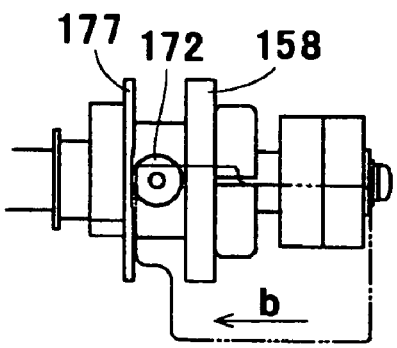
Figure 29C:
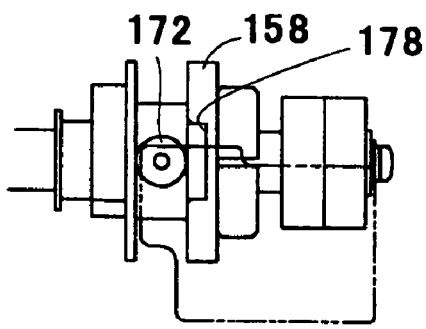
Figure 29D:
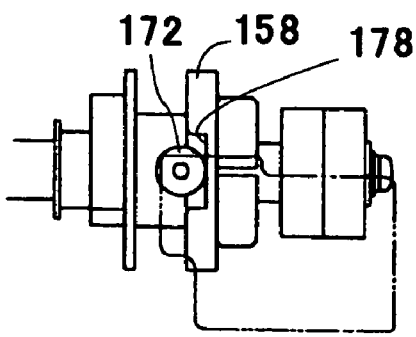
Figure 30A:
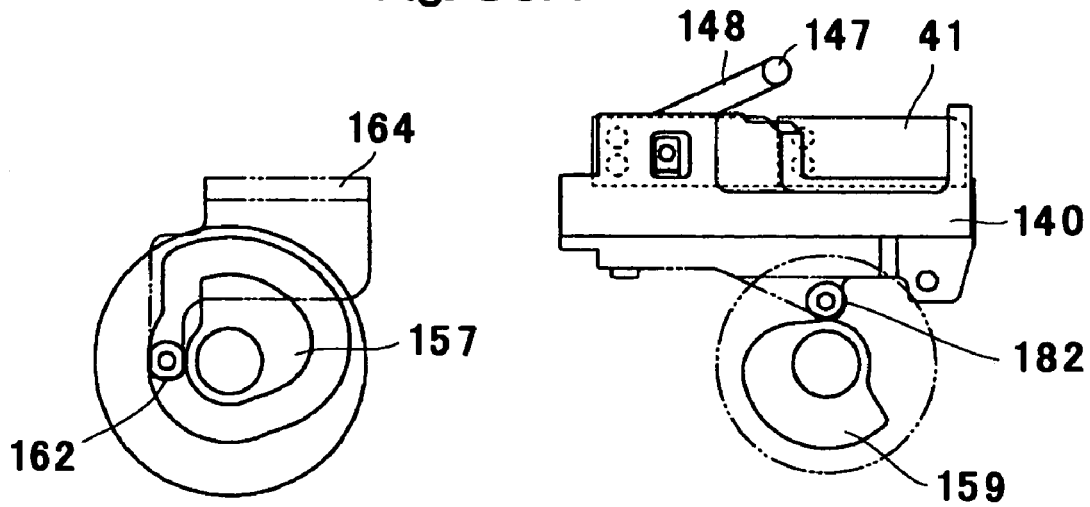
Figure 30B:
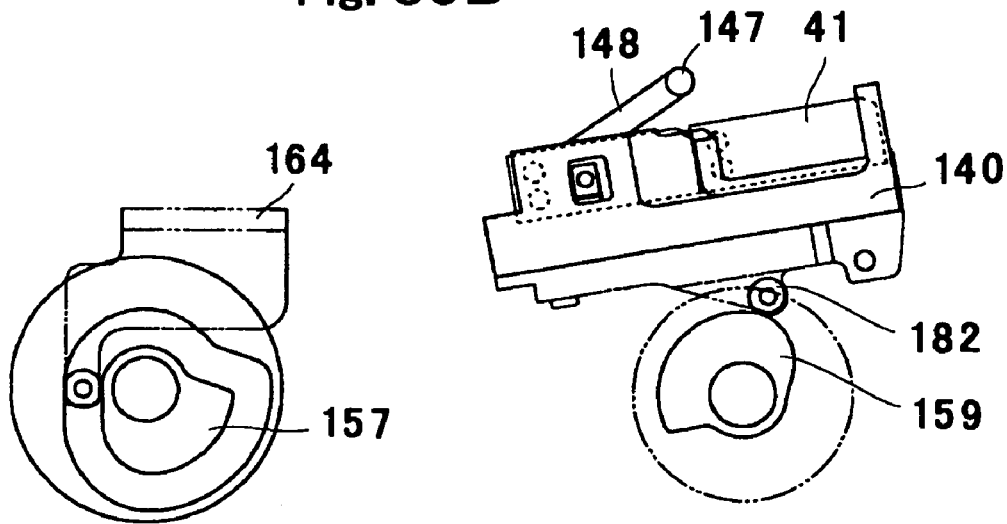
Figure 30C:
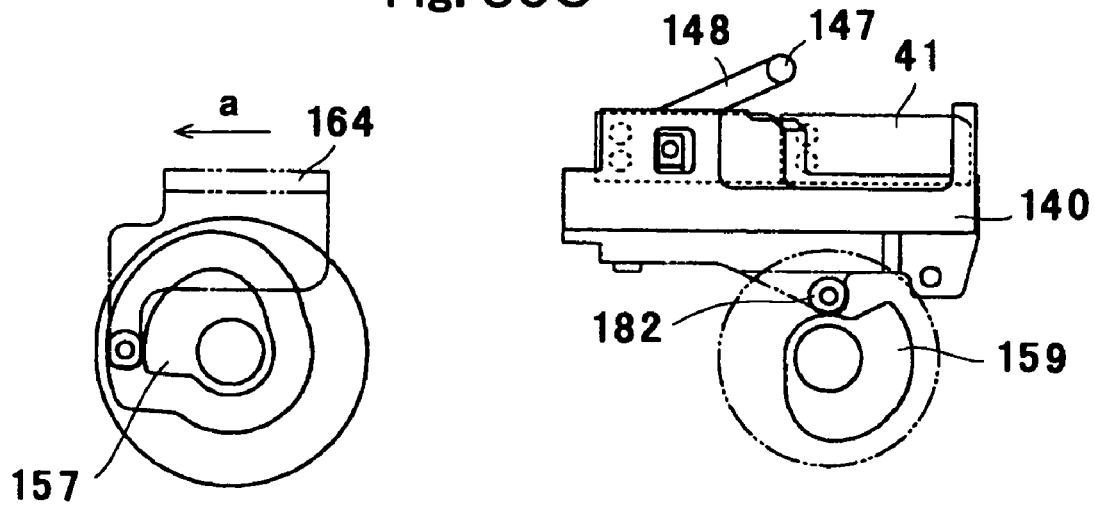
Figure 31:
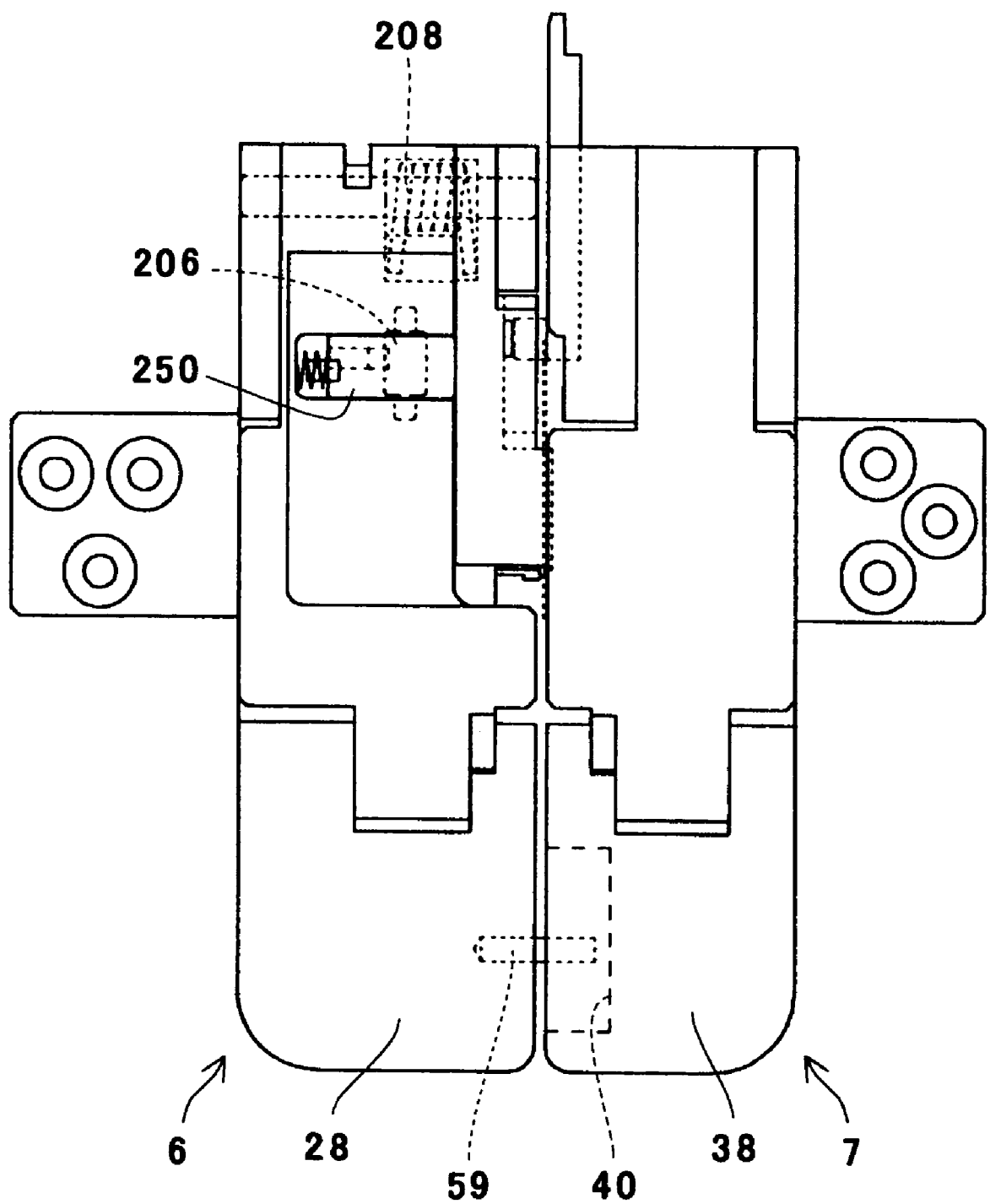
Figure 32:
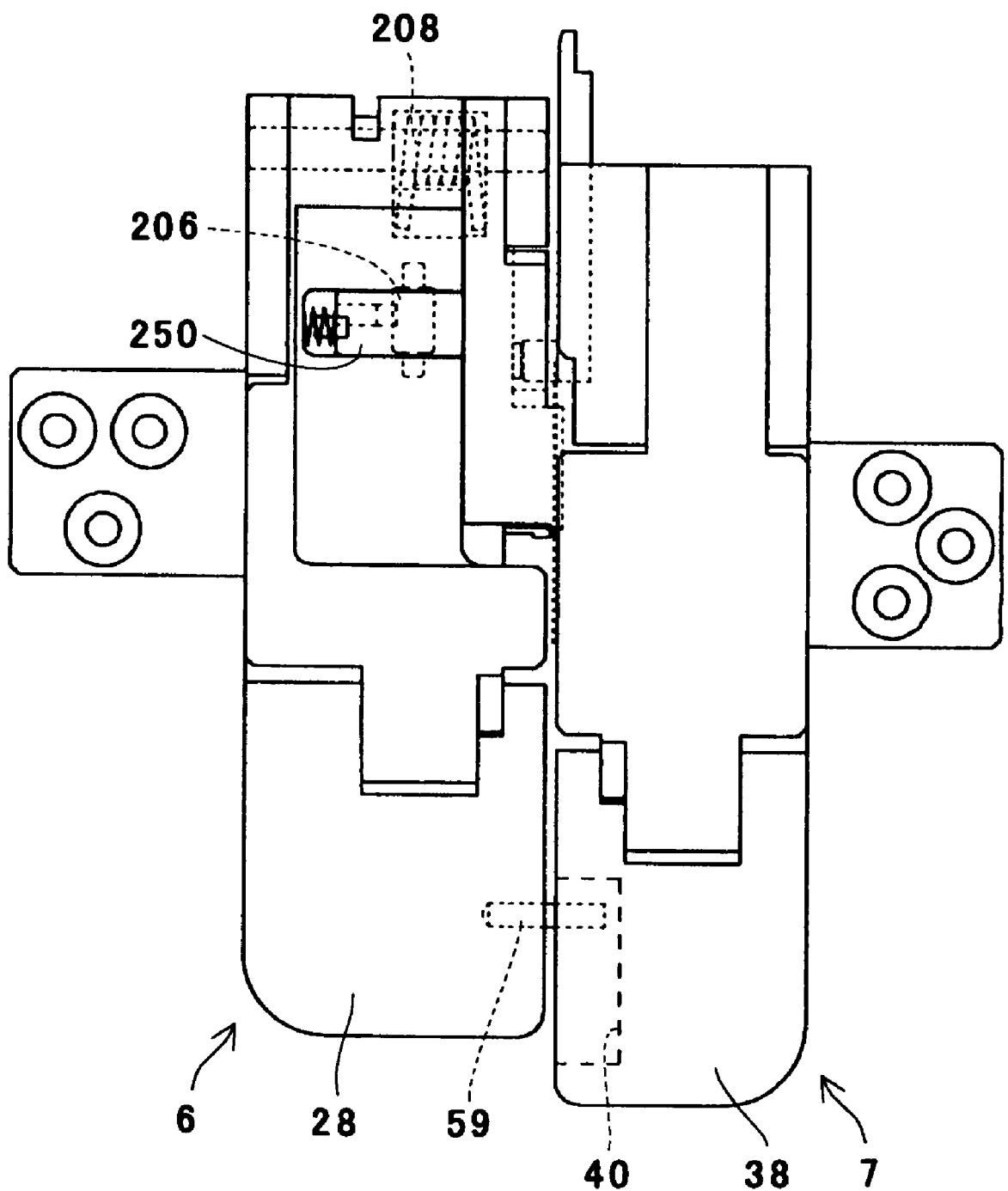

FIG. 22 is a side view showing evacuation movement of a tube-pushing member, FIG. 22A showing a state just before a tip portion of the tube-pushing member presses tubes to a flat state, FIG. 22B showing a state that the tip portion of the tube-pushing member presses the tubes to a flat state, and FIG. 22C showing a state that a wafer cuts the tubes held in a flat state;

FIG. 23 is a side view showing a state of evacuating the wafer from a cutting position by descending a holding member which holds the wafer;

FIG. 24 is a right side view showing the first clamp, tube-pushing member and wafer holder and showing a state that two tubes are held and pressed in a flat state;

FIG. 25 is a right side view showing the first clamp, tube-pushing member and wafer holder and showing a state that the two tubes are cut;

FIG. 26 is a right side view showing the first clamp, tube-pushing member and wafer holder, FIG. 26A showing a state that the tubes are held and pressed in a flat state, FIG. 26B showing a state that the tubes are cut and FIG. 26C showing a state that a covering body is opened;

FIG. 27 is a sectional front view showing the first clamp, tube-pushing member and wafer holder, FIG. 27A showing a state that the tubes are held and pressed in a flat state, FIG. 27B showing a state that the tubes are cut and FIG. 27C showing a state that the covering body is opened;

FIG. 28 is a partially broken plan view of the tube connecting apparatus showing a moving state of a wafer feeding member;

FIG. 29 is an enlarged plan view showing around a cum which regulates movement of the second clamp, FIG. 29A showing an initial state, FIG. 29B showing a finished state of connecting operation, FIG. 29C showing a state that the notched portion faces the bearing and FIG. 29D showing a state that the second clamp is moved to an evacuating position;

FIG. 30 is a side view of a cam which regulates movement of the first clamp and a cam which regulates movement of the wafer holder, FIG. 30A showing an initial state, FIG. 30B showing a cutting state, and FIG. 30C showing a state that cutting is finished or connecting is started;

FIG. 31 is a plan view of the first clamp and the second clamp showing a state that the two tubes are held and pressed in a flat state; and FIG. 32 is a plan view of the first clamp and the second clamp showing a state that the tubes are being connected or connecting thereof is finished.

DETAILED DESCRIPTION OF THE PREFERRED EMBODIMENTS

First Embodiment

<Structure>

Figure 1:
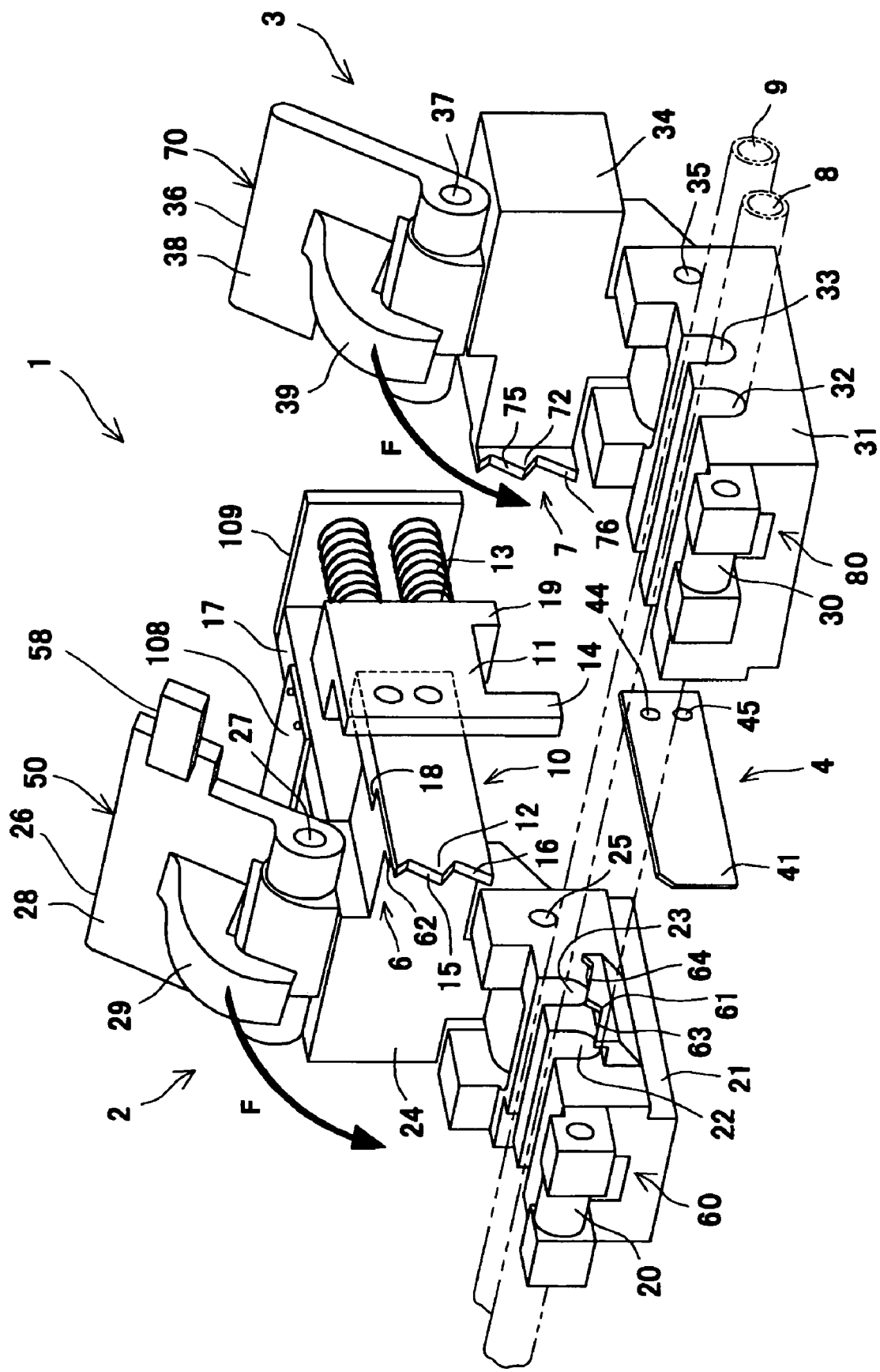
FIG. 1 is a perspective view showing main portions of a tube connecting apparatus in a first embodiment to which the present invention is applicable.

As shown in FIG. 1, a tube connecting apparatus 1 of the present embodiment is equipped with a first tube-holding assembly 2 serving as a first holding assembly and a second tube-holding assembly 3 serving as a second holding assembly both of which hold two flexible tubes 8, 9 approximately in a parallel state, a cutting mechanism 4 which melts the tubes 8, 9 by heat for cutting the tubes and which serves as a cutting unit. Further, the tube connecting apparatus 1 is equipped with a first clamp 6 which is provided at the first tube-holding assembly 2 to press the tubes 8, 9 to a flat state and which serves as a first pressing unit, a second clamp 7 which presses the tubes 8, 9 to a flat state and which serves as a second pressing unit, and a tube-pushing member 10 which is disposed between the first clamp 6 and second clamp 7 and adjacent to the first clamp 6 to press the tubes to a flat state and which serves as a third pressing unit.

The first clamp 6 has a first upper jaw portion 50 which forms an upper jaw of the first clamp 6 to press the tubes 8, 9 to a flat state and which serves as a first pressing section, and a first lower jaw portion 60 which forms a lower jaw of the first clamp 6 to support the tubes 8, 9 pressed to flat state by the first upper jaw portion 50 and which serves as a first supporting section. On the other hand, the second clamp 7 has a second upper jaw portion 70 which forms an upper jaw of the second clamp 7 to press the tubes 8, 9 to a flat state and which serves as a second pressing section, and a second lower jaw portion 80 which forms a lower jaw of the second clamp 7 to support the tubes 8, 9 pressed to flat state by the second upper jaw portion 70 and which serves as a second supporting section.

The tubes 8, 9 are made of soft resin such as, for example, soft polyvinyl chloride or the like and have flexibility, in which blood is contained and sealed. These tubes 8, 9 have approximately the same shape with respect to an inner diameter, an outer diameter and a length in a state before blood is contained and sealed. The first tube-holding assembly 2 has a holder 21 for holding the tubes 8, 9, and a covering body 24 which is fitted pivotably to a rear end portion of the holder 21 through a hinge 25 for opening and closing.

A pair of grooves 22, 23 which are parallel with each other and into which the two tubes 8, 9 are put (placed) are formed in the holder 21. A cross-section of the grooves 22, 23 is shaped as a letter U. It is preferable that a width of the grooves 22, 23 is set to have the same or a smaller width as/than a diameter of the tubes 8, 9 in an in artificial state. An operator pushes the tubes 8, 9 into inner sides thereof (downward direction) to put the tubes 8, 9 into the grooves 22, 23. The covering body 24, in a closed state, covers the grooves 22, 23 and has a function for fixing the tubes 8, 9 such that the tubes are put inside the grooves 22, 23 so as not to get rid of the grooves.

The first clamp 6 has a locking mechanism 26 for retaining the covering body 24 in a closed state. The locking mechanism 26 is constituted by a plate piece 28 which is fixed pivotably to a tip of the covering body 24 through a hinge 27, a pawl member 29 which is formed to protrude toward an inner face of the plate piece 28, and a stopping portion 20 which is formed at a front end of the holder 21. Accordingly, by pivoting the plate piece 28 in a direction of an arrow A in FIG. 1 to engage the pawl member 29 with the stopping portion 20 in a state that the covering body 24 is closed, the covering body 24 is locked so as not to open. For this reason, difficulties in cutting and connecting of the tubes are prevented since the covering body 24 is prevented from being opened unexpectedly during connecting of the tubes, and accordingly fixing (holding) to the tubes 8, 9 as well as pressing according to the first clamp 6 and the second clamp 7 are not canceled. Further, a rectangular solid shaped block 58 is fitted inside the plate piece 28 and the block 58 is protruded toward the second clamp 7.

Further, the first clamp 6 has a saw-shaped pressure closing member 61 which is fixed to a side face of the holder 21, and a saw-shaped pressure closing member 62 which is fixed to a side face of the covering body 24 and which bites the pressure closing member 61 each other. The pressure closing member 61 has inclined faces 63, 64 at positions corresponding to the grooves 22, 23 respectively, while inclined faces 65, 66, which are parallel to the inclined faces 63, 64 respectively and which are disposed at positions having a predetermined distance from the inclined faces 63, 64, are formed at the pressure closing member 62. (See FIG. 10.) Accordingly, when the covering body 24 is closed in a state that the tubes 8, 9 are put in the grooves 22, 23, the tube 8 is pressed by the inclined faces 63, 65 and the tube 9 is pressed by the inclined faces 64, 66 since the pressure closing members 61, 62 engage (bite) each other. According to the structure of the first clamp 6, dislocation (offset) or deformation of the tubes 8, 9 is restrained and easy and proper connection is secured when cut faces of the tubes 8, 9 are connected with each other, which will be stated later.

On the other hand, the second clamp 7 is disposed at a side of the first clamp 6 and adjacent to the first clamp 6 via the tube-pushing member 10. The second clamp 7, in the same manner as the first clamp 6, has a holder 31 at which a pair of grooves 32, 33 are formed and which holds the tubes 8, 9, a covering body 34 which pivots to the holder 31 for opening and closing, and a locking mechanism 36. A structure thereof corresponds to the first clamp 6. The locking mechanism 36 has a hinge 37, a plate piece 38 and a pawl member 39, and the holder 31 has a hinge 35 and a stopping portion 30.

The second clamp 7 has a saw-shaped pressure closing member 71 (unillustrated) which is fixed to a side face of the holder 31 and at a side of the holder 21, and a saw-shaped pressure closing member 72 which is fixed to a side face of the covering body 34 and at a side of the covering body 24 and which bites the pressure closing member 71 each other. The pressure closing member 71 has inclined faces 73, 74 at positions corresponding to the grooves 32, 33, respectively (See FIG. 10.) Inclined faces 75, 76, which are parallel to the inclined faces 73, 74 respectively and which are disposed at positions having a predetermined distance from the inclined faces 73, 74, are formed at the pressure closing member 72.

The first clamp 6 (the first tube-holding assembly 2) and the second clamp 7 (the second tube-holding assembly 3) are usually located such that the grooves 22, 32 correspond to (align) the grooves 23, 33 respectively each other.

The tube-pushing member 10 is connected with the first clamp 6 in a contact state at a side of the second clamp 7 and which is disposed movably and integrally with the first clamp 6 (the first tube-holding assembly 2). The tube-pushing member 10 has a saw-shaped tip portion 12 (corresponding to the pressure closing members 62, 72) at which inclined faces 15, 16 are formed in the same manner as the first clamp 6 and the second clamp 7. However, it differs from the first clamp 6 and the second clamp 7 in that it does not have the pressure closing members 61, 71 which bite each other via the tubes 8, 9. Further, the tip portion 12 of the tube-pushing member 10 is placed at a position protruded a little more than a position of the pressure closing member 62 of the first clamp 6, although the tip portion 12 has the same saw shape as the pressure closing member 62 of the first clamp 6 and the pressure closing member 72 of the second pressure closing member 72.

Further, the tube-pushing member 10 is always energized in a direction of a pressing position to the tubes 8, 9 by a pair of springs 13 which serve as an energizing section via a supporting member 11 which has a L shaped cross section and which is fixed to the tube-pushing member 10 by screws. An unillustrated U shaped slider is provided at the supporting member 11. This slider moves along an unillustrated rail being urged by or resisting energizing force of the springs 13 while slidably contacting the rail. Incidentally, the tube-pushing member 10 is integrated with the first tube-holding member 2 because the rail is fixed to a rail supporting member 17 which is fixed to the covering body 24 by screws.

The tube-pushing member 10 is disposed so as to contact the first clamp 6, however, it is movable relative to the first clamp 6 by an evacuation mechanism 100 (See FIG. 11.) which includes the springs 13 and which serves as an evacuation unit. Stepping portions 18 at which the first clamp 6 and the tube-pushing member 10 engage each other are respectively formed at the first clamp 6 and the tube-pushing member 10. When the covering body 24 is closed in a state that the tubes 8, 9 are put in the grooves 22, 23, movement of the tube-pushing member 10 is stopped in a direction of pushing the tubes 8, 9 by the stepping portion 18 of the first clamp 6 which serves as a first stopping member. Incidentally, since the tip portion 12 of the tube-pushing member 10 is protruded more than the pressure closing member 62 of the first clamp 6, the tip portion 12 pushes the tubes 12 prior to the first clamp 6 when the covering body 24 is closed.

Figure 4:
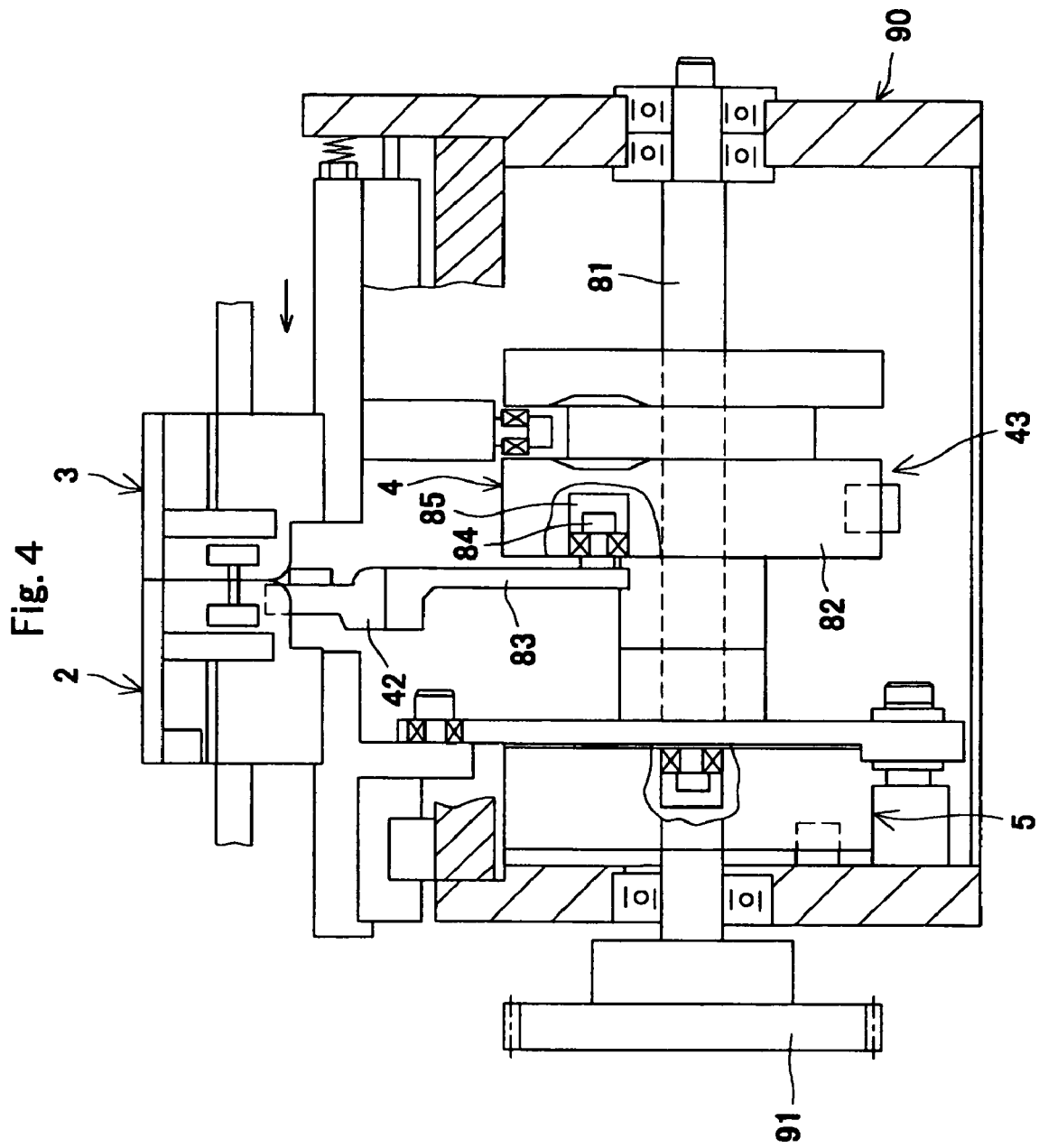
FIG. 4 is a partially broken plan view showing a first tube-holding assembly, a second tube-holding assembly and a cutting mechanism.

As shown in FIGS. 1 and 4, the cutting mechanism 4 is constituted by equipping a wafer (a cutting plate) 41 for melting and cutting the tubes 8, 9, a holding member 42 which holds the wafer 41 in an exchangeable manner and at which an aperture is formed and which serves as a cutting-plate holding section, and a cutting-plate movement mechanism 43 which moves the holding member 42 such that the wafer 41 inserts (advances) or evacuates (retreats) into/from a gap defined between the first tube-holding assembly 2 and the second tube-holding assembly 3 (the first clamp 6 and the second clamp 7).

A self-heating typed heat cutting plate can be used for the wafer 41. In such a wafer, a sheet of a metal plate such as a copper plate or the like is folded into two, and a resistance body having a desired pattern for heating is formed inside the folded metal plate via insulating layers. The wafer 41 has a structure that terminals 44, 45 disposed at both ends of the resistance body are exposed at apertures formed at each end portion of the metal plate.

When current is supplied between the terminals 44, 45 via an unillustrated current-carrying unit, the resistance body housed inside the wafer 41 generates heat and the wafer 41 is heated up to a temperature (ex. approximately 260 to 320 deg. C.) capable of melting and cutting the tubes 8, 9. Incidentally, it is preferable that the wafer 41 is disposable (for single use) at every connecting (joining) operation of the tubes. In this case, a structure may be employed that the wafer 41 to be held by the holding member 42 is replaced by a cutting-plate exchanging portion 46 (See FIGS. 2 and 3.) every time the tubes 8, 9 are connected.

The cutting-plate movement mechanism 43 is structured by equipping, as main parts, a cam 82 fitted to a rotation axis 81, an arm portion 83 extending downward the holding member 42, a following member 84 disposed at a tip of the arm portion 83 and extended to a side of the cam 82, fittings (unillustrated) to a main body 90, and an unillustrated hinge which supports the holding member 42 pivotably to the fittings. A cam groove 85 having a desired shape is formed at the cam 82 and the following member 84 is inserted into the cam groove 85 such that it can slide therein.

In accordance with rotation of the cam 82 according to rotation of the rotation axis 81, the following member 84 inserted into the cam groove 85 moves up and down, and the holding member 42 pivots around the unillustrated hinge. Accompanied by this movement, the holding member 42 rotates clockwise, and the wafer 41 in a heated state moves upward from an evacuated position and advances into the gap defined between the first tube-holding assembly 2 and the second tube-holding assembly 3, so that the tubes 8, 9 held by the grooves 22, 23 are melted and cut.

Figure 2:
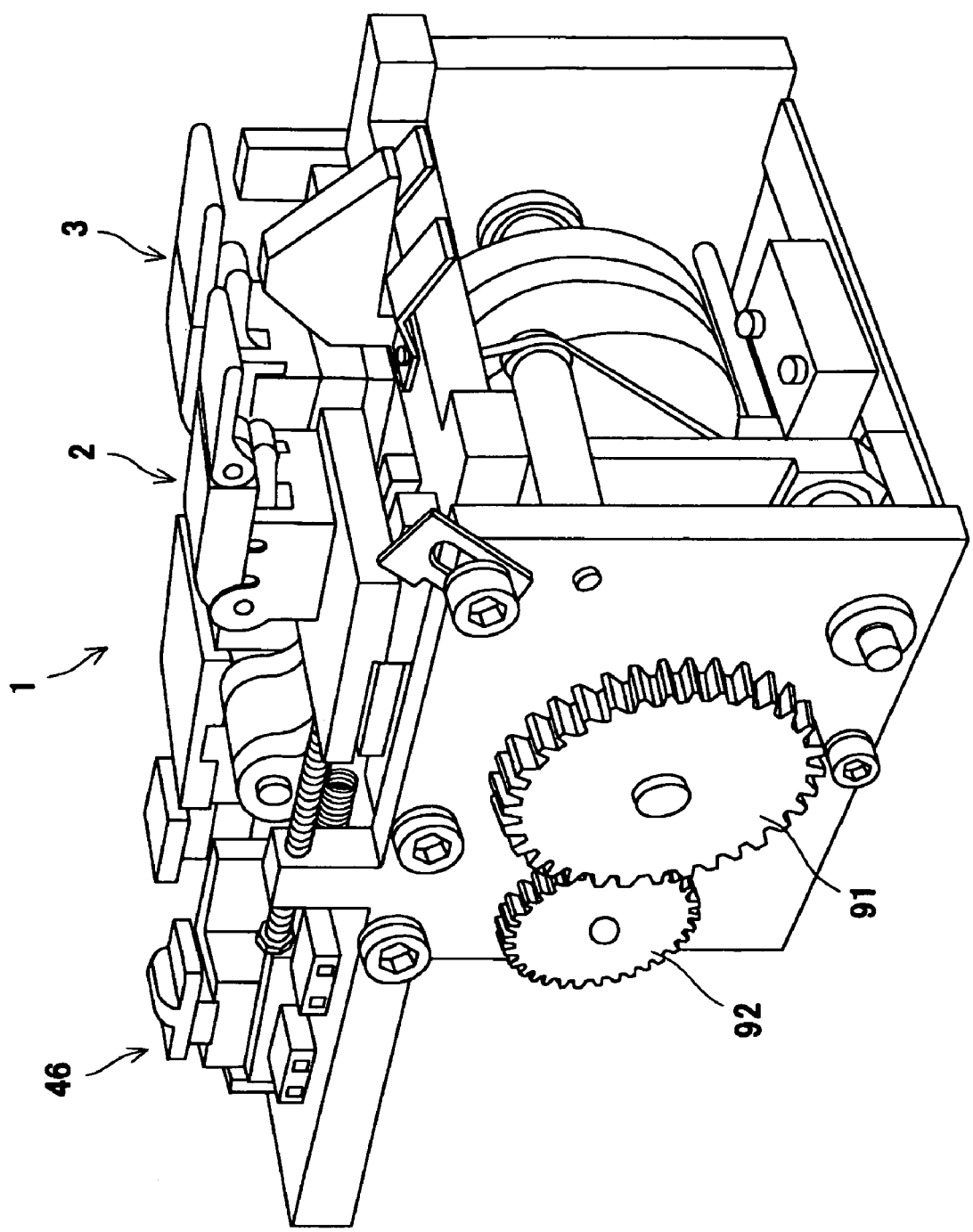
FIG. 2 is a schematic perspective view of the tube connecting apparatus in the first embodiment.
Figure 3:
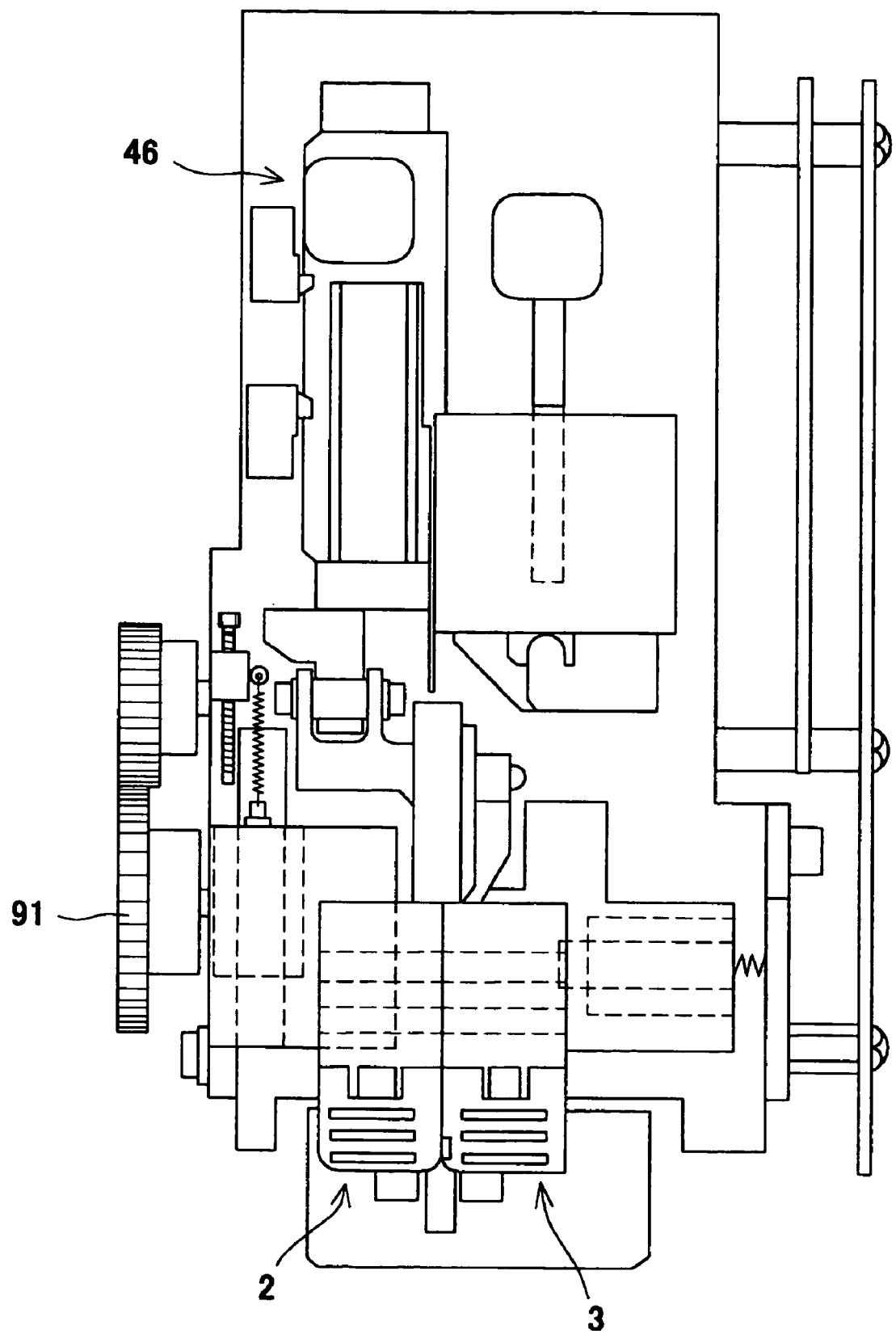
FIG. 3 is a plan view of the tube connecting apparatus in the first embodiment.

Both ends of the rotation axis 81 are supported by bearings pivotably to the main body 90 and a gear 91 is fitted to one end portion of the rotation axis 81. As shown in FIG. 2, the gear 91 bites a small-diameter gear 92 fitted to a rotation axis of an unillustrated motor each other. When the motor is driven, rotation force thereof is conveyed via the small-diameter gear 92 and the gear 91 to the rotation axis 81 for rotation.

Here, a relationship between vertical ascending of the wafer 41 and movement of the tube-pushing member 10 to an evacuating position will be explained briefly prior to a detailed explanation about the evacuation mechanism 100.

Figure 9A:
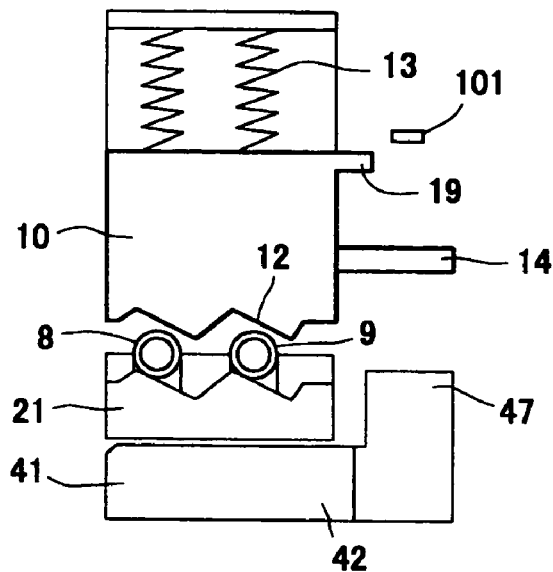
FIG. 9 is a side view showing evacuation movement of a tube-pushing member linked with movement of the cutting mechanism, FIG. 9A showing a state just before a tip portion of the tube-pushing member presses tubes to a flat state, FIG. 9B showing a state that the tip portion of the tube-pushing member presses the tubes to a flat state, and FIG. 9C showing a state that a cutting plate (a wafer) cuts the tubes held in a flat state.
Figure 9B:
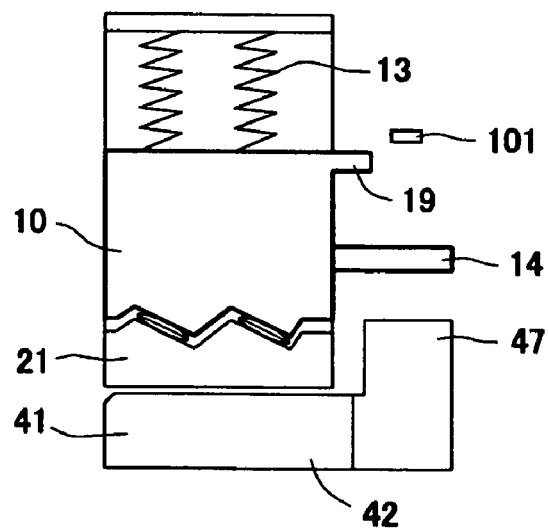

FIG. 9A shows a state just before the tip portion 12 of the tube-pushing member 10 presses tubes 8, 9 to a flat state after the covering body 24 of the first tube-holding assembly 2 is closed to the tubes 8, 9 set at (put in) predetermined positions (grooves 22, 23). As shown in FIG. 9B, when an operator continues closing operation of the covering body 24, the tip portion 12 of the tube-pushing member 10 presses the tubes 8, 9 to a flat state. At this time, pressing operation to the tubes 8, 9 according to the clamp 6 of the first tube-holding assembly 2 and the clamp 7 of the second tube-holding assembly 3 is also being carried out in a linked and continuous manner.

Figure 9C:
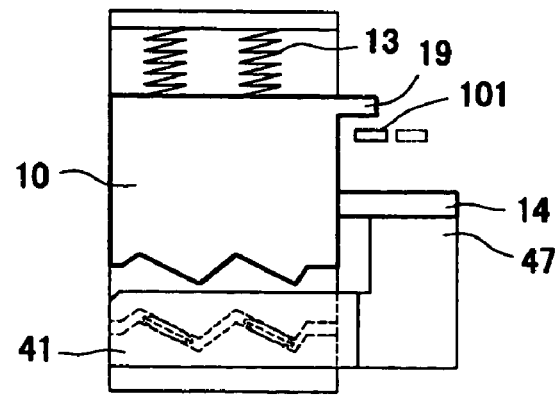

When an operator pushes an unillustrated start button disposed at the tube connecting apparatus 1 after the pressing operation to the tubes 8, 9 is finished, the cutting-plate movement mechanism 43 is activated at a predetermined timing. Accompanied by ascending movement of the holding member 42, a first projection portion 47 (a first projection member) which is formed at a back face of the holding member 42 pushes up a second projection portion 14 (a second projection member) which is formed at a part of the holding member 11 integrally formed with the tube-pushing member 10 while resisting energizing force of the springs 13 to locate the tube-pushing assembly 10 at a predetermined evacuating position. Linked with the ascending movement of the holding member 42, the wafer 41 which is in a heated state and which is held by the holding member 42 melts by heat and cuts the tubes 8, 9 which are held in a flat state by the first clamp 6 and the second clamp 7. (A state shown in FIG. 9C) In this state, a holding state to the tubes 8, 9 by the first clamp 6 and the second clamp 7 is being kept. At this time, a lever member 101, which is constituted as a part of the evacuation mechanism 100 for the tube-pushing member 10 and which regulates the energizing force of the springs 13 to stop downward movement of the tube-pushing member 10 and which serves as a part of a second stopping member, moves to engage a convex portion 19 which is formed at a part of the holding member 11 integrally formed with the tube-pushing member 10, which enables the tube-pushing member 10 to locate at the predetermined evacuating position. Further, in a state shown in FIG. 9C, when cutting operation according to the wafer 41 to the tubes 8, 9 is finished, operation for moving the cut tubes 8, 9 relatively to face end portions of the tubes to be connected each other, which will be stated later, is carried out at a predetermined timing in a state that the wafer 41 is located at the cutting position.

Figure 10:
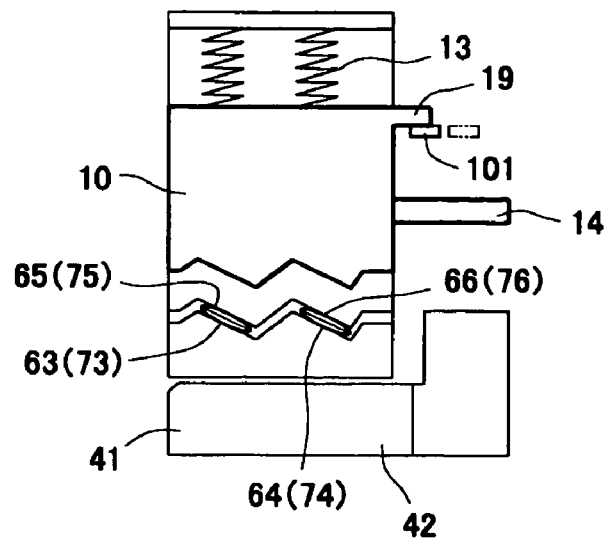
FIG. 10 is a side view showing a state of evacuating the wafer from a cutting position by descending a holding member which holds the cutting plate.

Next, as shown in FIG. 10, the holding member 42 which holds the wafer 41 descends to evacuate the wafer 41 from the cutting position at a predetermined timing (at a predetermined position where the following member 84 slides along a shape of the cam groove 85 in accordance with rotation of the cam 82 in a case that the cam 82 is used as stated above.) The tube-pushing member 10 is kept located at the evacuating position according to a function of a lever member 101, which allows connecting operation for closely contacting the end portions to be connected of the tubes which are placed to face each other. Incidentally, the operation for closely contacting and connecting the tubes is synchronized with the descending evacuation movement of the wafer 41.

Figure 11A:
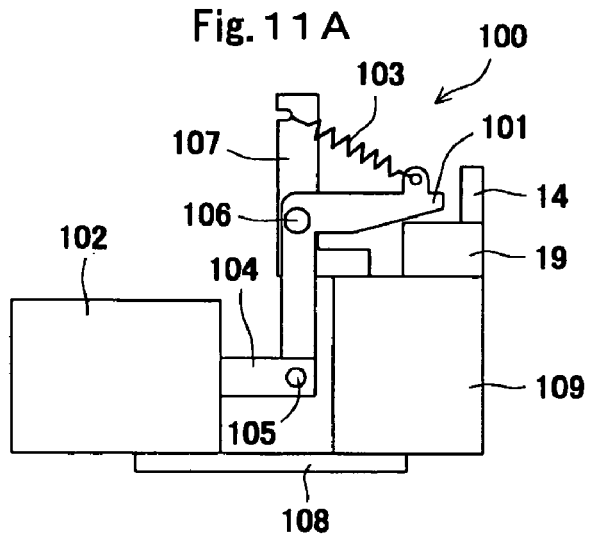
FIG. 11 is a plan view of an evacuation mechanism, FIG. 11A showing a state of allowing the tube-pushing member to press the tubes without activating the evacuation mechanism, FIG. 11B showing a state of holding the tube-pushing member at an evacuating position by activating the evacuation mechanism.
Figure 11B:
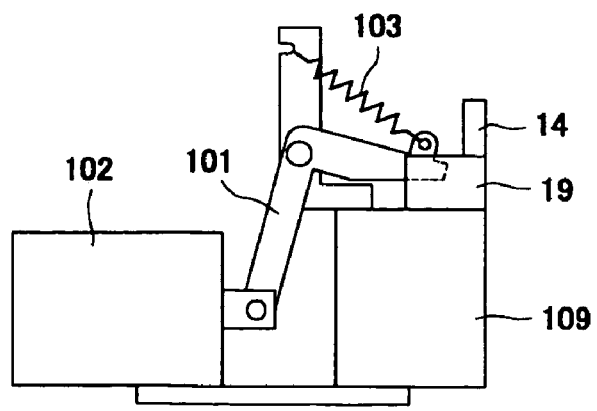

FIG. 11A shows a state of allowing the tube-pushing member 10 to press the tubes 8, 9 without activating the evacuation mechanism 100, and FIG. 11B shows a state of holding the tube-pushing member 10 at the evacuating position by activating the evacuation mechanism 100.

The evacuation mechanism 100 is constituted mainly by the lever member 101 which movable to engage the convex portion 19 formed at a part of the tube-pushing member 10 as stated above, an actuator and a solenoid 102 serving as a part of a second stopping member both of which move the lever member 101 to an engaging position with the convex portion 19, and a tensile spring 103 which moves the lever member 101 so as to release the lever member 19 from a state of engaging the convex portion 19 when the solenoid 102 is switched off to cancel magnetization.

The lever member 101 is shaped as a letter L. One end side of the lever member 101 is connected with a plunger 104 of the solenoid 102 via a node 105. The tensile spring 103 is connected to a hole which is formed at another end side of the lever member 101 and which is adjacent to the engaging position with the convex portion 19. The lever member 101 moves to pivot around a rotation axis 106. The lever member 101 is fitted to a fitting member 107 by a screw provided at the rotation axis 106. The solenoid 102 is fixed to an anchor member 108 by screws. Incidentally, both of the fitting member 107 and the anchor member 108 are fixed by screws to the rail supporting member 17 which is fixed by screws to an upper plate 109 at which a pair of the springs 13 are bridged to the supporting member 11. According to mutual installation of these parts, the tube-pushing member 10 as well as the evacuation mechanism 100 are fixed integrally to the first tube-holding assembly 2.

Further, the tube connecting apparatus 1 is equipped with a movement mechanism 5 which moves the first tube-holding assembly 2 and the second tube-holding assembly 3 respectively in a predetermined direction and which serves as a movement unit. The movement mechanism 5 is constituted by a first movement mechanism (unillustrated) which moves the first tube-holding assembly 2 in a row direction of the tubes 8, 9 to the second tube-holding assembly 3 (a direction of an arrow X in FIG. 8 and an opposite direction thereto), and a second movement mechanism (unillustrated) which moves the second tube-holding assembly 3 in a direction that the second tube-holding assembly 3 approaches/separates to/from a side of the first tube-holding assembly 2. Such a movement mechanism can be structured, for example, by employing stepping motors, and the technique disclosed in the JPA 6-91010 or known techniques may be applicable. Incidentally, a second embodiment stated later refers to the details of such a movement mechanism.

Incidentally, the tube connecting apparatus 1 has a controlling unit structured with a CPU, a ROM, a RAM, an interface and the like at a downward position of the cutting-plate exchanging portion 46, and it is accommodated in an unillustrated casing such that the gear 91, the small-diameter gear 92 and protruded members as shown in FIG. 2 are hidden.

(Operation)

Next, operation of the tube connecting apparatus 1 in this embodiment will be explained.

First, an operator carries out operation for setting the tubes 8, 9 to the grooves 22, 23, then closing the covering body 24 of the first tube-holding assembly 2 and the covering body 34 of the second tube-holding assembly 3 to the set tubes 8, 9.

(See FIG. 5.) When the operator further continues to carry out the operation for closing the covering body 24, the tip portion 12 of the tube-pushing member 10 firstly abuts and then deforms the tubes 8, 9, which are put in a parallel state at a first position P1 that is an abutting position, to a flat state. (See FIG. 6A.) At this time, blood inside the tubes 8, 9 at a portion which was pressed by the tube-pushing member 10 is pushed out such that it is excluded in directions of an arrow a and an arrow b in FIG. 6A.

Subsequently, when the operation for closing the covering body 24 is carried out further, the pawl member 29 engages the stopping portion 20 at the locking mechanism 26 in the first tube-holding assembly 2, thereby the covering body 24 is locked so as not to open. In this state, the first clamp 6 presses and holds the tubes 8, 9 to/in a flat state with predetermined pressing force at a second position P2 which is adjacent to the first position P1. At this time, the tube-pushing member 10 disposed so as to contact the first clamp 6 also presses the tubes 8, 9 to an almost squashed state (a state that blood inside the tubes hardly exits) according to the energizing force of the springs 13 in the same manner as the first clamp 6. (See FIG. 6B.)

Then, when operation for closing the covering body 34 perfectly is carried out by the operator such that the pawl member 39 engages the stopping portion 30 at the locking mechanism 36 in the second tube-holding assembly 3 and the covering body 34 is locked so as not to open, the second clamp 7 which is disposed so as to contact the tube-pushing member 10, in the same manner as the first clamp 6, presses and holds the tubes 8, 9 to a flat state in a state that the tubes are almost squashed (a state that blood inside the tubes hardly exists) at a third position P3 which is adjacent to the first position P1 and which is a position opposing to the second position P2 via the first position P1 with predetermined pressing force. Thus, blood inside the tubes 8, 9 from the second position P2 to the third position P3 via the first position P1, namely, blood inside the tubes 8, 9 at portions being equivalent from a portion pressed by the first clamp 6 to a portion pressed by the second clamp 7 via the tube-pushing member 10 is almost excluded. (See FIG. 6C.) Pressing and holding operation of the tubes 8, 9 is finished with the foregoing process, and operation is shifted to the tube-cutting process.

When an operator pushes the start button of the apparatus 1, the heated wafer 41 ascends at a predetermined timing and the tube-pushing member 10 which pressed the tubes 8, 9, at the first position P1 cancels pressing thereto and ascends while resisting the energizing force of the springs 13. Both continue ascending movement, and the wafer 41 advances to a gap between the second position P2 and the third position P3 to melt and cut the tubes 8, 9. At this time, the tube-pushing member 10 is located at the evacuating position. (See FIG. 7A.)

Subsequently, the first tube-holding assembly 2 having the first clamp 6 is driven to move by a predetermined amount in a direction of an arrow X in FIG. 8 by the above mentioned first movement mechanism to move (change) positions of the cut tubes 8, 9 relatively such that the end portions to be connected of the tubes face each other. At this time, the wafer 41 which cut the tubes 8, 9 is retained at its cutting position in a stopped state.

Next, the wafer 41 descends to leave the cutting position. However, the tube-pushing member 10 is retained at the evacuating position as stated above. (See FIG. 7B.) Synchronizing with descending movement of the wafer 41, the second tube-holding assembly 3 having the second clamp 7 is driven to move by the second movement mechanism a predetermined amount (the cut tubes 8, 9 are moved relatively) in a direction of an arrow Y in FIG. 7C which is a direction approximately orthogonal to the arrow X in FIG. 8. Thereby, the facing ends of the tubes contact closely each other, and the tube connecting (process) is finished. (See FIG. 7C.)

Moving amounts in the X and Y directions according to this embodiment will be explained in detail. The moving amount of the first tube-holding assembly 2 in the direction of the arrow X in FIG. 8 is set to 7.62 mm, and the moving amount of the second tube-holding assembly 3 in the direction of the arrow Y in FIG. 7C is set to 0.6 mm. In other words, 7.62 mm set for the moving amount of the first tube-holding assembly 2 is equivalent to a width length of the tubes 8, 9 which are put approximately in a parallel (row) state. 0.6 mm for the moving amount of the second tube-holding assembly 3 was set through various tests. Namely, the test results for attaining the best connecting state were obtained by setting to 0.9 mm as a separated distance between the first clamp 6 and the second clamp 7 interposing the wafer 41 having a thickness of 0.28 mm at the time of cutting the tubes 8, 9, by setting to 0.3 mm as an interval (a gap) between the first clamp 6 and the second clamp 7 at the time of closely contacting and connecting the cut tubes 8, 9, and by setting to 0.6 mm as a moving amount of the second tube-holding assembly 3 which is a pushing amount at the time of connecting the tubes.

Figure 12A:
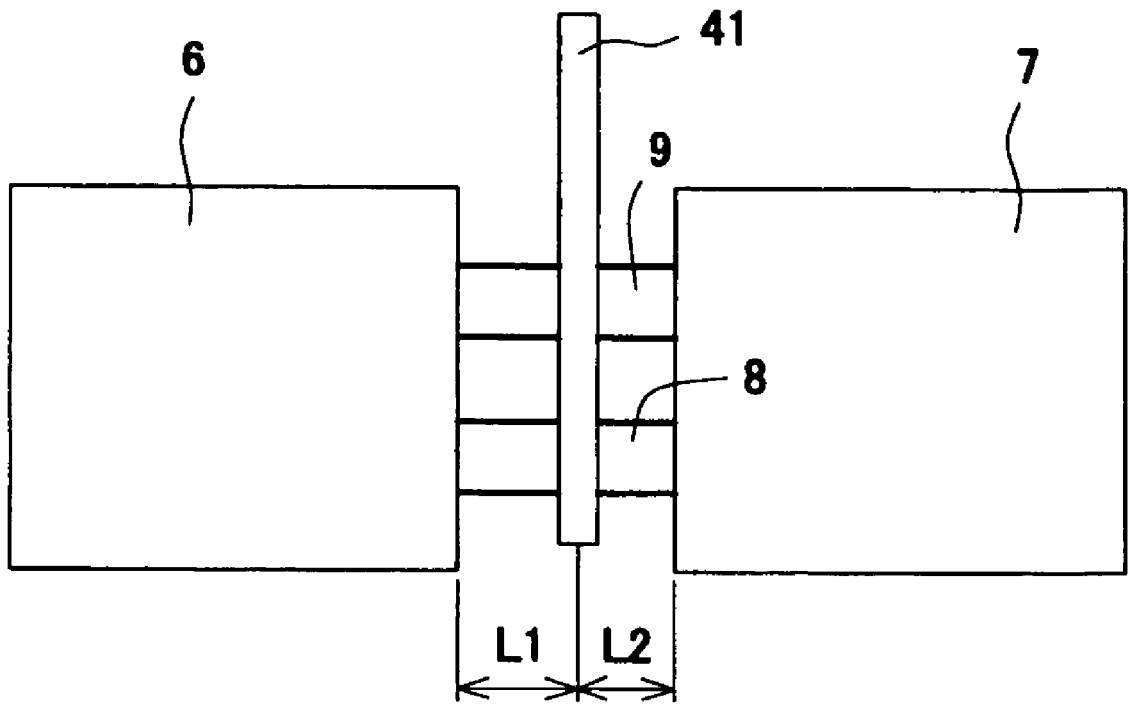
FIG. 12 is a plan view showing the first clamp, second clamp and cutting mechanism in the connecting process, FIG. 12A showing a relationship in a distance at a time of cutting the tubes and FIG. 12B illustratively showing side faces of the wafer at a time of moving the tubes in a direction of an arrow A in FIG. 8.

Further, as shown in FIG. 12A, in a state that the tubes 8, 9 are cut by the wafer 41, a distance L2 between the second clamp 7 and the wafer 41 is set to 0.117 mm while a distance L1 between the first clamp 6 and the wafer 41 is set to 0.45 mm. In short, the distance between the first clamp 6 and the wafer 41 is set to be larger than the distance between the second clamp 7 and the wafer 41. Incidentally, in FIG. 12A, both of the distances L1 and L2 are illustrated as distances from a position of a center line of the wafer 41 without taking a thickness of the wafer 41 into account.

(Effects and the Like)

Next, effects and the like of the tube connecting apparatus 1 in this embodiment will be explained.

As stated above, in the tube connecting apparatus 1 of this embodiment, the tube-pushing member 10 having the tip portion 12 which is protruded a little more than the pressure closing member 62 of the first clamp 6 is disposed between the first clamp 6 and the second clamp 7 which press the tubes 8, 9 to a flat state, and prior to pressing according to the first clamp 6 and the second clamp 7, the tube-pushing member 10 presses the tubes 8, 9 to push out and exclude blood inside the tubes at the pressing position. Accordingly, the tube connecting apparatus 1 can connect the tubes each other without being influenced by the blood in the tubes at the time of cutting and then connecting the tubes.

However, because a little blood remains at the end portions in the width direction of the tubes 8, 9 which were squashed to the flat state when the tubes 8, 9 were pressed (squashed) to exclude blood between the first clamp 6 and the second clamp 7. It was confirmed by tests that most of residual liquid existed at around a center portion between the first clamp 6 and the second clamp 7 in the length direction of the tubes 8, 9 when the wafer 41 advanced to cut the tubes 8, 9 at the same time that the tube-pushing member 10 canceled pressing operation thereof and ascended upward. If most of this residual liquid remains around the end portions to be connected, connecting, strength (fusion strength) of the tubes drops. Particularly, in a case that the liquid inside the tubes 8, 9 is blood, since the connecting strength becomes weaker because blood components such as protein and the like remain there without vaporization, it is necessary to exclude the residual liquid existing around there.

Figure 12B:
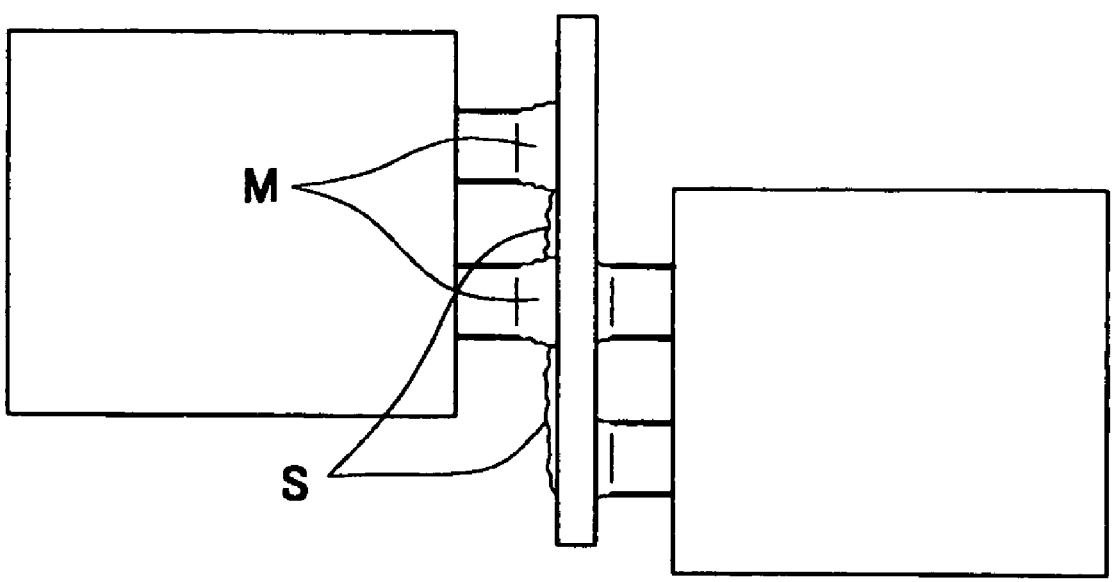

According to the tube connecting apparatus 1 of this embodiment, the first tube-holding assembly 2 having the first clamp 1 is driven to move by the predetermined amount in the direction of the arrow X in FIG. 8 by the first movement mechanism which moves the first tube-holding assembly 2 so as to move the positions of the cut tubes 8, 9 relatively to face the end portions of the tubes each other. At that time, in this embodiment, the end portions of the tubes 8, 9 are moved so as to slidably contact the heated wafer 41. Under a concept that a part around the end portions is melt further by heat, the distances among the first clamp 6, the second clamp 7 and the wafer 41 are set such that the distance between the first clamp 6 provided at the first tube-holding assembly 2 which moves the end portions to be connected of the tubes so as to face each other and the wafer 41 is set to be larger than that of another. Thus, the tube connecting apparatus 1 can realize stable and reliable tube connecting by further melting thermally around the center portion of the tubes (portion of reference M in FIG. 12B) where the residual blood exists to exclude the residual liquid at the time of moving the tubes. Therefore, according to the tube connecting apparatus 1 of this embodiment, a large effect that the tubes in which blood is contained and sealed are connected stably and reliably can be obtained. It should be noted that blood components such as protein and the like in the excluded residual liquid adhere to the side faces of the wafer 41 with which the tubes contacted at the time of moving the tubes as shown in FIG. 9B. (See reference S in FIG. 12B.)

Further, the tube connecting apparatus 1 of this embodiment can realize wet-to-wet connecting between the tubes easily and rapidly under a sterilized condition only by putting the tubes 8, 9 in which blood is contained and sealed into the grooves 22, 23, 32 and 33 and locking the covering bodies 24, 34 with the locking mechanisms 26, 36. Because such a tube connecting apparatus has been requested to realize from a public view, an industrial value thereof seems to be extremely high.

Incidentally, in this embodiment, an example that the tube-pushing member 10 is disposed movably to and integrally with the first tube-holding assembly 2 was shown. However, even if the tube-pushing member 10 is disposed movably to and integrally with the second tube-holding assembly 3, the same effects as those of this embodiment can be obtained. In such a structure, stepping portions at which the second clamp 7 and the tube-pushing member 10 engage each other may be formed respectively at the second clamp 7 and the tube-pushing member 10. Further, in this embodiment, an example that the lever member 101 is moved to the engaging position with the convex portion 19 by the solenoid 102 was shown, however, a motor, for example, such as a liner motor or the like may be used for such an actuator.

Furthermore, in this embodiment, such a structure that the holding member 42 pivots around the unillustrated hinge to ascend the wafer 41 in order to melt and cut the tubes 8, 9 was exemplified, however, the present invention is not limited to the same. For example, a structure that the holding member 42 ascends in a vertical direction to ascend the wafer 41 vertically in order to melt and cut the tubes 8, 9 may be employed.

Moreover, in this embodiment, as the evacuation mechanism 100, a structure for holding the tube-pushing member 10 at the evacuating position was exemplified, however, a structure for moving the tube-pushing member 10 to the evacuating position, namely, a structure for evacuating the tube-pushing member 10 may be added (ex. the first projection portion 47 or the like which is formed at a part of the holding member 42 and which pushes up the second projection portion 14 which is formed at a part of the tube-pushing member 10 to locate the tube-pushing member 10 to the predetermined evacuating position).

Further, in this embodiment, an example that the first movement mechanism and the second movement mechanism, which constitute the movement mechanism 5, move the assemblies respectively in one direction of the X direction or Y direction (and opposite direction thereto) was shown. However, the present invention is not confined to the same. A tube connecting apparatus may be structured in a manner that the mechanism moves the assemblies two-dimensionally or three-dimensionally. Such a structure enables sooner tube connecting.

Second Embodiment

Next, a second embodiment of a tube connecting apparatus that cuts and then connects two tubes in which blood is contained and sealed and that the present invention is applied to will be explained. This embodiment has a latch which stops the tube-pushing member at the evacuating position, a mechanism for canceling the latch, and a linking mechanism for linking the first and second clamps. Further, in this embodiment, a wafer feeding mechanism, a movement mechanism for moving the first and second clamps, a wafer moving (melting) mechanism and CPU control for tube connecting, which were not referred to in the first embodiment, will be explained in detail. Incidentally, in this embodiment, the same parts or members as those in the first embodiment are denoted by the same reference numerals and explanations thereof will be omitted, and only different parts or members will be explained.

<Structure>

Figure 14:
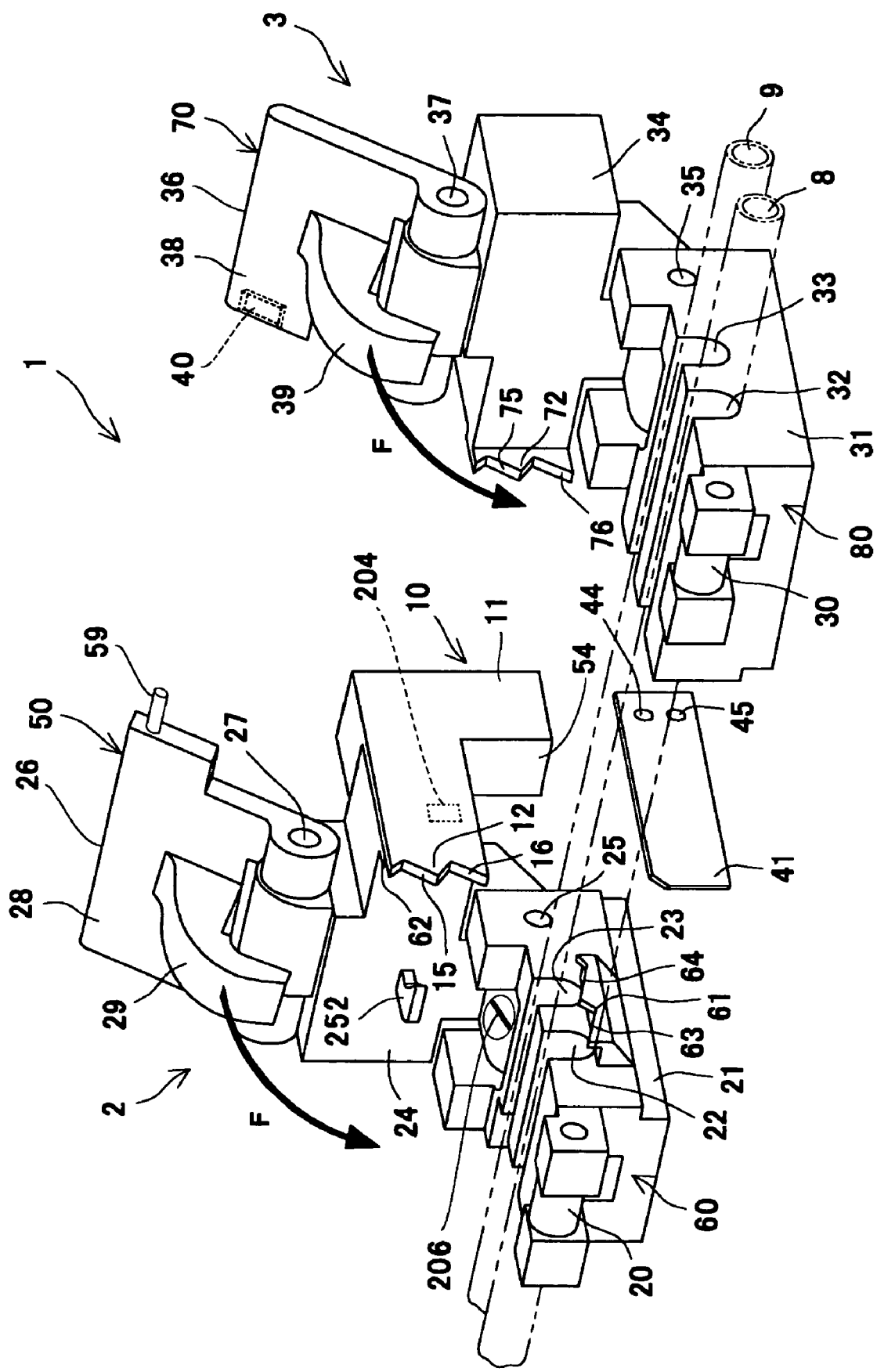
FIG. 14 is a perspective view showing clamps of the tube connecting apparatus in the second embodiment.

As shown in FIG. 14, a shaft 59 which protrudes toward a side of the second clamp 7 and which serves as a protruded portion is fixed to an end face of the plate piece 28 of the first clamp 6 in this embodiment, in place of the block 58 in the first embodiment. Further, a slot 40 into which the shaft 59 can be inserted and which serves as a groove portion or a dented portion is formed at an end face of the plate piece 38 of the second clamp 7 and at a side of the first clamp 6. This slot 40 has a function of allowing the shaft 59 to move in accordance with movement of the first clamp 6 in tube connecting operation as stated later. (See FIGS. 31 and 32.) Incidentally, the tube connecting apparatus us accommodated in a casing such that protruded members as shown in FIG. 14 are hidden. (See FIG. 15.)

A supporting member 11 having a L shaped cross section is fixed by screws to the tube-pushing member 10 of this embodiment. The supporting member 11 has a pillar-shaped supporting member projection portion 54 which projects downward. Incidentally, a slider is provided at the supporting member 11 in the same manner as the first embodiment, and the slider is constituted so as to move along a rail. The rail is fixed to a rail supporting member (not shown) and the rail supporting member is fixed by screws to the covering body 24. For this reason, the tube-pushing member 10 is integrated with the first clamp 6 and movable relative to the first clamp 6. Incidentally, in the same manner as the first embodiment, since the tip portion 12 of the tube-pushing member 10 is protruded more than the pressure closing member 62 of the first clamp 6, the tip portion pushes the tubes 8, 9 prior to the first clamp 6 when the covering member 24 is closed.

Here, with reference to a relationship between the tube-pushing member 10 and the first clamp 6, the latch 250 which stops (locates) the tube-pushing member 10 at the evacuation position and which serves as a stopping unit, and a roller 206

(a roller member) which cancels stopping (engagement) according to the latch 250 and which serves as a cancellation unit, both of which are features of this embodiment, will be explained.

As shown in FIGS. 24 and 25, the latch 250 having an approximately T shape is provided at an interior of the covering body 24 of the first clamp 6. The tip portion 251 of the latch 250 pivots around a fulcrum shaft 203 in accordance with ascending of a wafer holder 140 (See FIGS. 15 and 16.) which serves as a cutting-plate holding section as stated later to advance into a groove portion 204 which is formed at the ascending tube-pushing member 10 for engagement. Thereby, the tube-pushing member 10 is located at the evacuating position. Further, the latch 250 has a cylinder-shaped rear end portion 252 which is extended downward. The rear end portion 252 is formed so as to protrude from the covering body 24 of the first clamp 6 (See FIG. 14.) and is able to advance, according to closing operation of the covering body 24, into a hole which is formed at a part of a supporting member 205 disposed at a lower side of the first clamp 6.

The roller 206 made of resin is disposed at the hole formed at the supporting member 205. When tube connecting operation is finished and the covering body 24 is opened upward to remove the tubes from the apparatus as stated later, the roller 206 in a stopped state functions to push an inclined face 257 (See FIGS. 27A and 27B.) which is formed at a side (a side of the tube-pushing member 10) of the rear end portion 252 of the latch 250 along the inclined face. In other words, the inclined face 257 of the cylinder-shaped rear end portion 252 of the latch 250 runs away gradually due to abutment with the roller 206. Then, the tip portion 251 of the latch 250 comes out of a stopping (engaging) state with the groove portion 204 formed at a part of the tube-pushing member 10. Thereby, the tube-pushing member 10 is released from the stopping state at the evacuating position and drops downward to return to an initial state. (See FIGS. 26C and 27C.) In short, the roller 206 functions as a cancellation unit which cancels a stopping function of the latch 250 served as a stopping unit.

Incidentally, a torsion coil spring 208 which always energizes the tube-pushing member 10 downward, namely, to a side of the tubes 8, 9, is provided at the fulcrum shaft 203. Further, a compression spring 209, which energizes the latch 250 to a side of the tube-pushing member 10 and which serves as an energizing unit, is provided adjacent to a side of the tip portion 251 of the latch 250.

Figure 15:
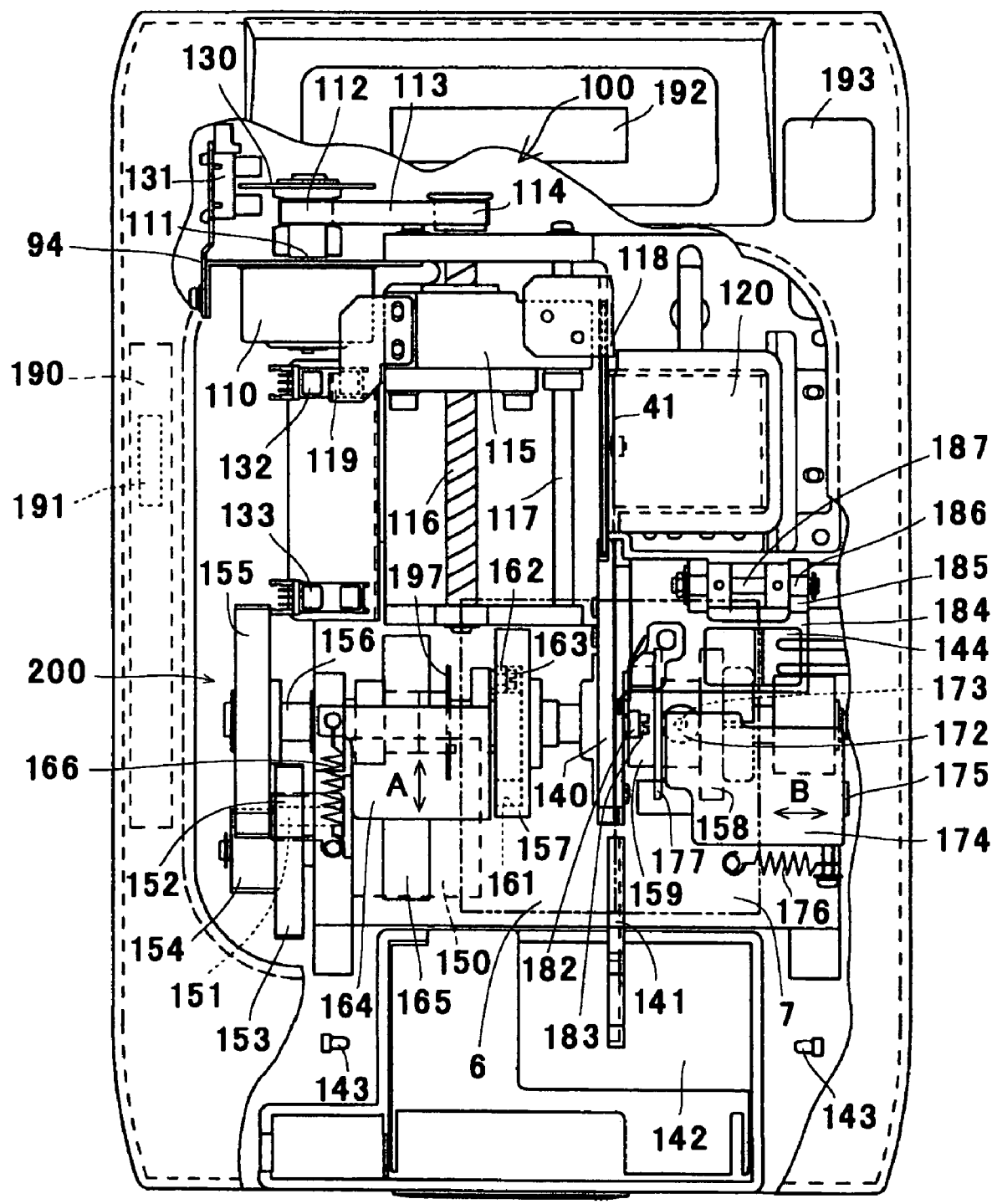
FIG. 15 is a partially broken plan view of the tube connecting apparatus in the second embodiment.

Further, as shown in FIG. 15, the tube connecting apparatus 1 is equipped with a wafer feeding mechanism 170 which feeds the wafer 41.

A fitting member 94 is set up at the casing of the tube connecting apparatus 1 and a pulse motor 110 capable of normal and reverse rotation is fixed by screws to the fitting member 94. A gear 112 is fixed to an output shaft 111 of the pulse motor 110, and a timing belt 113 is entrained between the gear 112 and a gear 114. The gear 114 is disposed at an axis of a ball screw 116 on which a wafer feeding member 115 that feeds the wafer 41 capable of cutting the tubes 8, 9 one by one is provided and that is called as a shuttle. An unillustrated nut which engages the ball screw 116 is provided at an interior of the wafer feeding member 115. For this reason, the wafer feeding member 115 moves along the ball screw 116 due to rotation of the ball screw 116 in accordance with rotation of the gear 114 of which driving source is the pulse motor 110. One side of the wafer feeding member 115 is supported by a rod-shaped shaft 117 to stabilize posture (movement) of the wafer feeding member 115 at the time of feeding the wafer. A feeding piece 118 which feeds the wafer 41 accommodated in a wafer cassette 120 which accommodates a plurality of wafers 41 (70 pieces in this embodiment) one by one from the wafer cassette 120 in accordance with movement of the wafer feeding member 115 is fixed at an end portion of the wafer feeding member 115.

Unillustrated compression springs are disposed at an interior of the wafer cassette 120 so as to energize the wafers 41. When the wafer 41 is fed by the feeding piece 118 of the wafer feeding member 115, an adjacent wafer faces a side of the wafer feeding member 115 one after another, which allows the feeding piece 118 to feed the wafer 41 continuously. Incidentally, the wafer feeding member 115 can move in a direction opposite to a direction of feeding the wafer 41 according to reverse rotation of the pulse motor 110.

Further, a revolving plate 130 which is adjacent to the gear 112 and which has a plurality of slits and which rotates according to rotation of the pulse motor 110 is fixed to an end portion of the output shaft 111 of the pulse motor 110. The revolving plate 130 is provided to detect a moving amount of the wafer feeding member 115. At the vicinity of the revolving plate 130, a transmission type sensor 131 which detects a revolving amount of the revolving plate 130 is fixed by screws to the fitting member 94 at an opposite side of the gear 114 so as to stride the revolving plate 130.

A transmission type sensor 132 which detects the wafer feeding member 115 which is located at a feeding start position of the wafer 41 and a transmission type sensor 133 which detects the wafer feeding member 115 which is located at a feeding end position of the wafer 41 are disposed separately with a predetermined interval at an opposite side of the wafer cassette 120 via the ball screw 116. A piece to be detected 119 having an approximately L shape is fixed to the wafer feeding member 115 at an opposite side of the feeding piece 118. Incidentally, detection of the moving amount of the wafer feeding member 115 according to the above stated revolving plate 130 and the transmission type sensor 131 is carried out at an interval between both positions of the transmission type sensors 132, 133.

Figure 16:
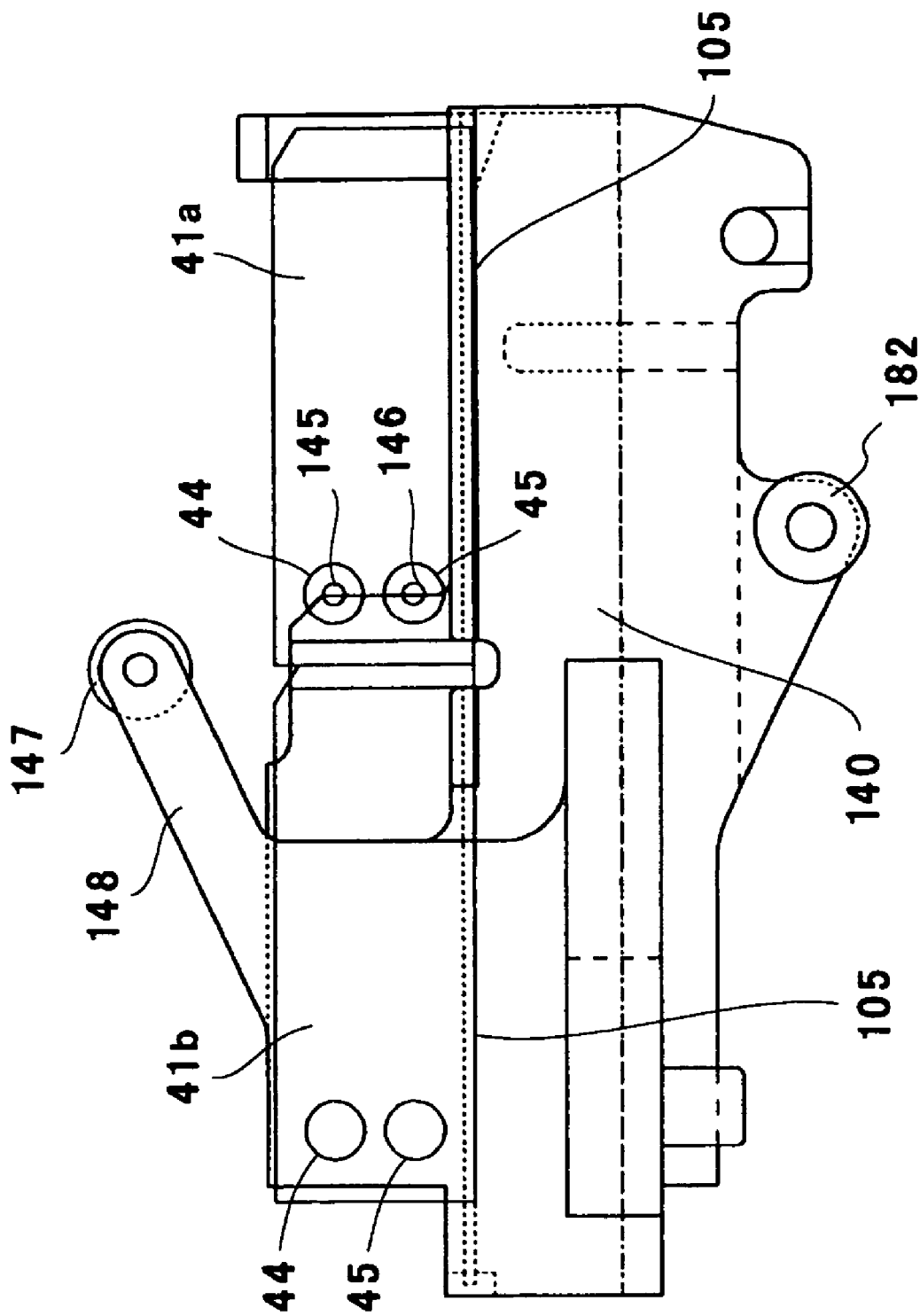
FIG. 16 is an enlarged side view of a wafer holder.

The wafer 41 fed by the wafer feeding member 115 is located to a downstream side of a wafer conveying path from the wafer cassette 115, then located inside the wafer holder 140 which holds the wafer 41 and which constitutes a part of a cutting unit. As shown in FIG. 16, in this embodiment, a structure that two pieces of the wafer 41 are held in the wafer holder 140 such that end faces thereof contact each other is employed. Namely, the wafer 41 is supplied in a manner that a wafer 41a fed formerly from the wafer cassette 120 is pushed and moved on a conveying path 105 in the wafer holder 140 by a wafer 41b fed newly from the wafer cassette 120. In other words, the wafer 41b pushes and advances the wafer 41a forward, and the wafer 41a is located at a position for cutting the tubes 8, 9 in the wafer holder 140.

The terminals 44, 45 for the wafer 41a which is located at a forward side in the wafer holder 140 are supplied with electricity by projection-shaped electrode portions 145, 146 from an unillustrated power unit via a harness of which illustration is omitted. The electrode portions 145, 146 are fixed integrally to the wafer holder 140 and are disposed so as to face via the wafer 41 to an end surface of one wall side (a back side in FIG. 16) of the wafer holder 140. Incidentally, as stated later, because the wafer holder 140 moves up and down (swings) at the time of cutting the tubes 8, 9, the electrode portions 145, 146 integrally fixed to the wafer holder 145, 146 also have a structure capable of supplying electricity for heating to the wafer 41.

The resistance body inside the wafer 41 generates heat according to electricity supply from the electrode portions 145, 146, and the wafer 41 is heated up to the temperature capable of melting and cutting the tubes 8, 9 in the same manner as the first embodiment. Further, the wafer feeding mechanism 170 has a structure capable of exchanging the wafer 41 held in the wafer holder 140 every time the tubes 8, 9 are connected.

The wafer holder 140 is heated by a heater 144 which is fitted to a pivot-supporting plate 184 which will be stated later. (See FIG. 15.) While electric power is supplied to the heater 144 from the unillustrated power unit, the wafer holder 140 always keeps a heated state during a period that electric power is supplied to the tube connecting apparatus 1. An unillustrated temperature sensor such as a thermistor or the like which detects a temperature of the wafer holder 140 is fixed to the wafer holder 140, and the wafer holder 140 is controlled to keep a predetermined temperature (70 deg. C. in this embodiment).

Temperature controlling in this embodiment will be explained further. Since a surface of the wafer 41 is covered by the copper plate as stated above, the wafer 41 is influenced by the temperature that the wafer holder 140 has due to the material (copper) characteristics when it is inserted into the wafer holder 140 and it reaches the predetermined temperature immediately after it is inserted into the wafer holder 140. A controlling unit 190 as stated later forecasts that the wafer 41 supplied electric power from the electrode portions 145, 146 reaches a predetermined temperature (ex. about 260 to 320 deg. C. which is the same as the first embodiment) after a predetermined period of time from a time that the wafer 41 is inserted into the wafer holder 140 in order to shift to tube-cutting operation according to the wafer 41 (ascending movement of the wafer holder 140).

Figure 17:
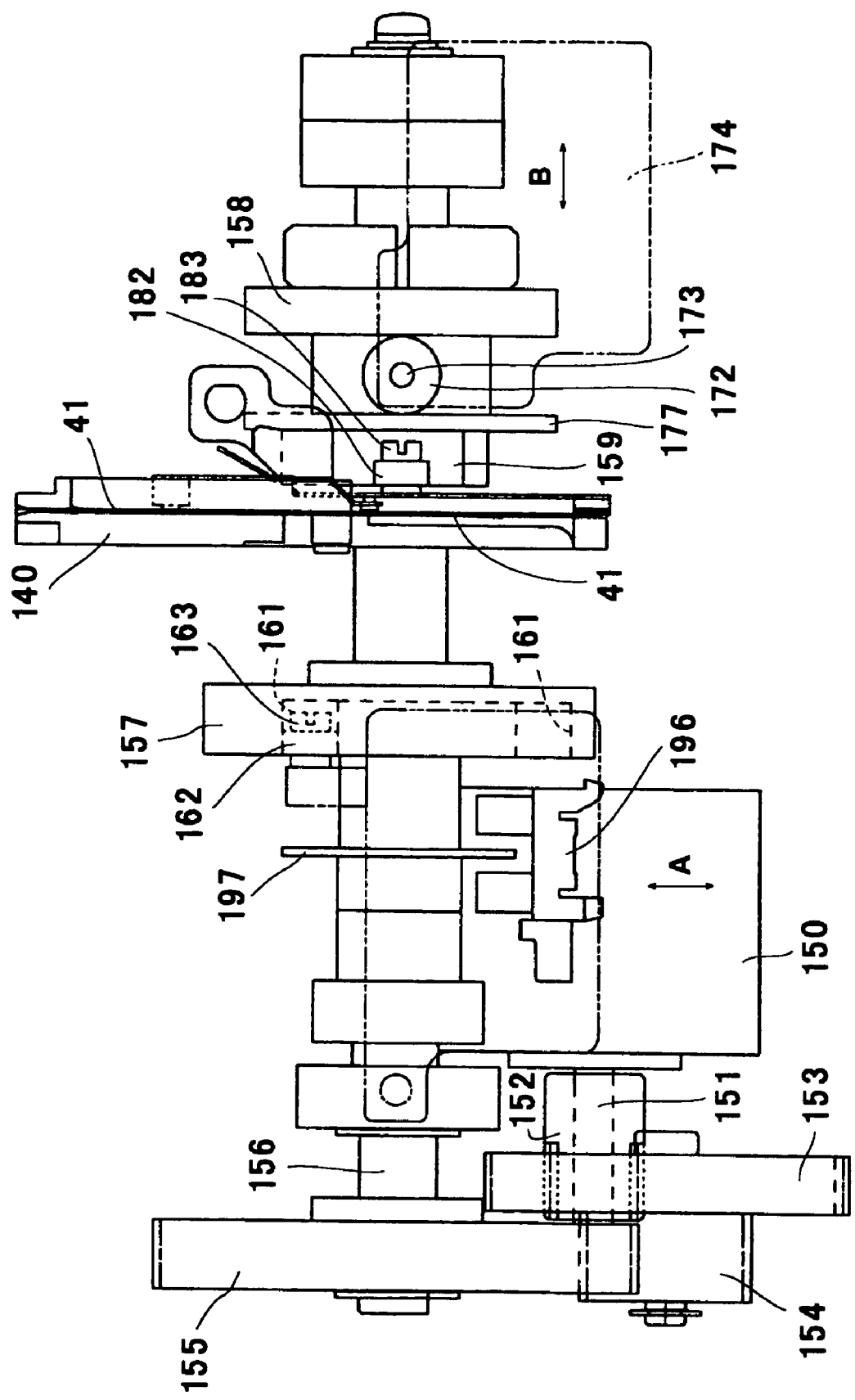
FIG. 17 is an enlarged plan view of a drive-conveying mechanism.

As shown in FIGS. 15 and 17, the tube connecting apparatus 1 is equipped with a drive-conveying mechanism 200 that functions as a part of a movement unit which moves the first clamp 6 and the second clamp 7 and that moves the wafer holder 140 (up and down) and functions a part of a cutting unit and a cutting-plate movement section.

A pulse motor 150 which is a driving source of the drive-conveying mechanism 200 and which is capable of normal and reverse rotation is fitted by screws to an unillustrated motor fitting member which is fixed to the casing of the tube connecting apparatus 1 at a side of the wafer holder 140 and at a downstream side of the wafer feeding member 115. A gear 152 is fixed to an output shaft 151 of the pulse motor 150 and the gear 152 bites a gear 153 each other. A gear 154 is fixed on a coaxial line of the gear 153 and this gear 154 bites a gear 155 each other. A driving shaft 156 which rotates together with the gear 155 according to driving force conveyed to the gear 155 and which serves as a part of a movement unit and a part of a cutting-plate movement section is provided at a center of rotation for the gear 155. A cam 157 which regulates movement of the first clamp 6, a cam 158 which regulates movement of the second clamp and a cam 159 which regulates movement of the wafer holder 140 are respectively fixed on the driving shaft 156. Accordingly, driving force from the pulse motor 150 is conveyed to the driving shaft 156 and the cams 157, 158 and 159 are driven to rotate respectively.

Figure 13:
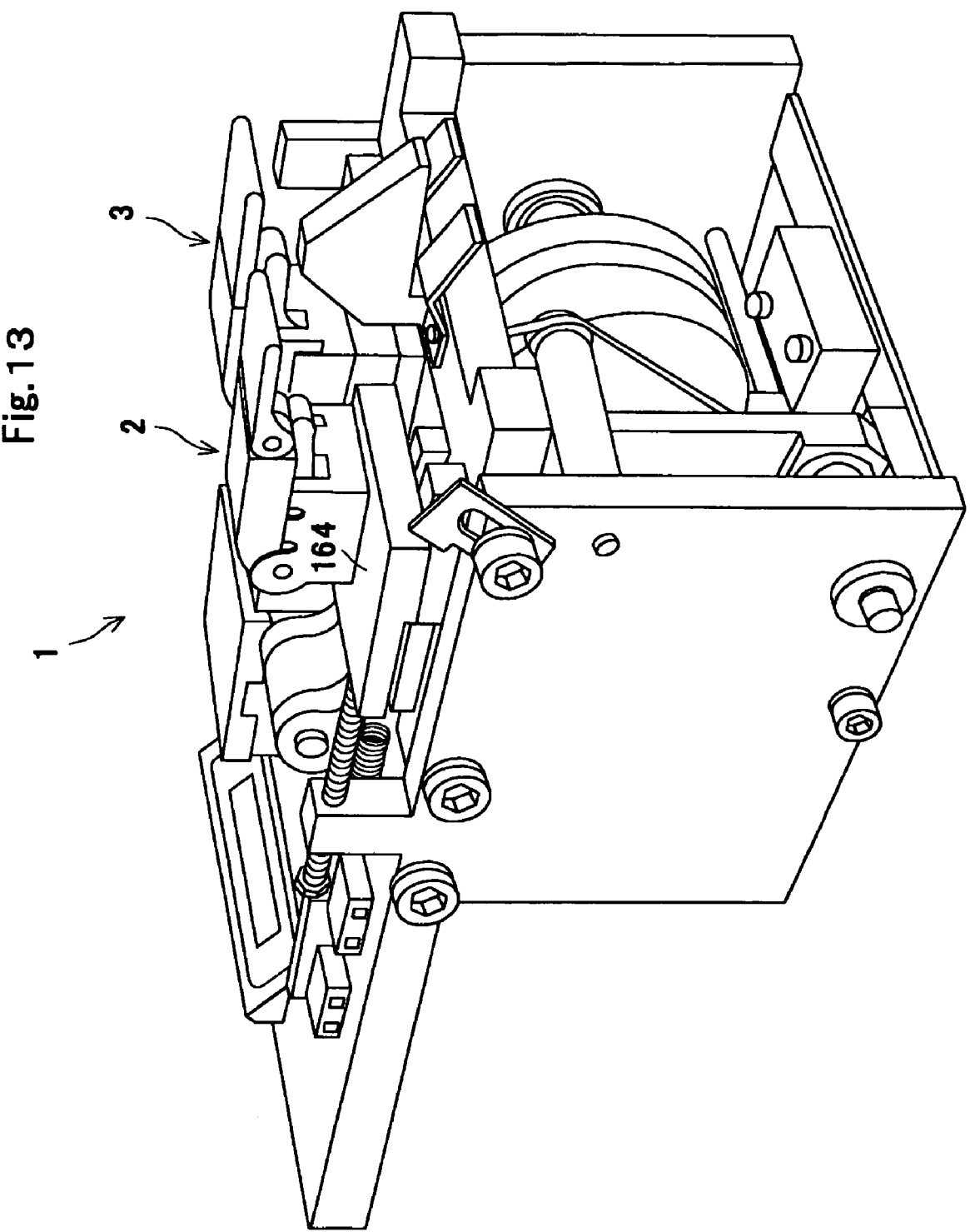
FIG. 13 is a schematic perspective view of a tube connecting apparatus in a second embodiment to which the present invention is applicable.

A groove 161 is formed at an interior of the cam 157, and a bearing 162 which engages an edge face of the groove 161 is connected via a fitting member 163 to a supporting table 164 (See FIG. 13.) which supports the first clamp 6 in a fixed state. For this reason, the bearing 162 slides along the edge face of the groove 161 formed at the interior of the cam 157 to enable the first clamp 6 to move in a predetermined direction (a direction of an arrow A in FIG. 15). Incidentally, a liner guide 165 which guides the supporting table 164 (the first clamp 6) so as to move stably is disposed at a bottom portion of the supporting table 164 in a contact state. Further, a compression spring 166 is bridged at one end of the supporting member 164 so as to energize this supporting member 164 to a predetermined direction.

On the other hand, a bearing 172 which engages a surface of the cam 158 is connected via a fitting member 173 to a supporting table 174 which supports the second clamp 7 in a fixed state. For this reason, according to rotation of the cam 158, the bearing 172 slides along the surface of the cam 158 to enable the second clamp 7 to move in a predetermined direction (a direction of an arrow B in FIG. 15). Incidentally, in this embodiment, the bearing 172 is constituted to not only engage a side face of the cam 158 but also engage a surface of a flange portion 177 which is integrally formed with the cam 159 which regulates the movement of the wafer holder 140. In short, the bearing 172 is located between the side face of the cam 158 and the flange portion 177 so that the bearing 172 has a structure capable of engaging and sliding on both of them, and the flange portion 177 is included in a part of a function of the cam 158 which regulates the movement of the second clamp 7. A notch portion 178 (See FIGS. 29C and 29D.) which is a characteristic structure in this embodiment is formed at a part of the cam 158 as stated later. Incidentally, a liner guide 175 which guides the supporting table 174 (the second clamp 7) so as to move stably is disposed at a bottom portion of the supporting table 174 in a contact state. Further, a compression spring 176 is bridged at one end of the supporting member 174 so as to energize this supporting member 174 to a predetermined direction.

Further, a bearing 182 (See FIG. 16.) is fitted via a fitting member 183 to a bottom portion of the wafer holder 140. Because the bearing 182 slides along a surface shape of the cam 159 according to rotation of the cam 159, the wafer holder 140 is constituted so as to move in a predetermined direction (a vertical direction). In other words, by pivoting integrally with and around a shaft axis 187 which penetrates a hole 186 formed at a protruded portion 185 of the pivot-supporting member 184 which is fitted to the wafer holder 149, the wafer holder 140 is structured so as to be able to swing in a vertical direction. A slanted projection portion 148 which has a metal roller 147 at its tip is integrally formed with an upper side of the wafer holder 140 (See FIG. 16.), and the roller 147 is brought to contact the supporting member projection portion 54 (See FIG. 14.). Due to a change in the surface shape of the cam 159, when the wafer holder 140 ascends (swings) at a predetermined timing, the tube-pushing member 10 is pushed upward. Thus, the projection portion 148 functions as an evacuation guiding unit which guides the tube-pushing member 10 to the evacuating position.

Further, a revolving plate 197 at which a notch 198 is formed is fixed to the driving shaft 156 between the cam 157 and the gear 155. (See FIG. 18.) Transmission type sensors 195, 196 are disposed adjacent to the revolving plate 197 so as to stride the revolving plate 197. By utilizing the notch 198 formed at the revolving plate 197, position detection for the first clamp 6 and the second clamp 7 is carried out by the transmission type sensors 195 and 196. Namely, while the revolving plate 197 rotates in a predetermined direction according to rotation of the driving shaft 156, when light from the transmission type sensor 195 transmits the notch 198 (See FIG. 18A.), the first clamp 6 and the second clamp 7 are defined at their initial positions. Thus, the transmission type sensor 195 is used as a sensor for detecting the initial positions of the first clamp 6 and the second clamp 7.

As shown in FIG. 15, a guide 141 which guides (constitutes the conveying path for) a used wafer 41 and a waste box 142 which accommodates the used wafer(s) 41 are disposed at a downstream side of the wafer holder 140. The wafer 41 located at a position at which it can cut the tubes is wasted (accommodated) to the waste box 142 after cutting and connecting operation of the tubes 8, 9 is carried out. This wasting operation is also carried out by pushing the end faces of the wafers 41 each other as stated above. The wasted wafer 41 is guided along the guide 141 and then dropped into the waste box 142 to accommodate it. A transmission type sensor 143 which detects a full state of the used wafers 41 wasted and accommodated in the waste box 142 is disposed at a side of the waste box 142 and at a position having a predetermined height from a bottom of the waste box 142.

Furthermore, the tube connecting apparatus 1 is equipped with a controlling unit 190 for carrying out movement controlling of whole of the apparatus, a display panel 192 for displaying a state of the apparatus to an operator, a start button 193 for starting movement/operation of the apparatus, a constant voltage power supply unit which converts commercial AC power source to DC power source which can drive/actuate actuators such as pulse motors and the like as well as the controlling unit 190.

The controlling unit 190 is constituted with a CPU 191 which operates at a high clock speed as a central processing unit, a ROM in which controlling program and controlling data are memorized, a RAM which works as a work area for the CPU 191 and an internal bus which connects these. An external bus is connected to the controlling unit 190. A display controlling section which controls display of the display panel 192, a start button controlling section which controls a start command from the start button 193, a sensor controlling section which controls signals from various sensors such as transmission type sensors, temperature sensors and the like, an actuator controlling section which controls motor drivers which sends driving pulses to pulse motors are connected to the external bus. Incidentally, the display panel 192, the start button 193, the above-stated various sensors, the pulse motors 110, 150 are connected respectively to the display controlling section, the start button controlling section, the sensor controlling section and the actuator controlling section.

<Operation>

Next, with respect to operation of the tube connecting apparatus 1 in this embodiment, operation carried out by the CPU 191 in the controlling unit 190 will be explained.

When power source is inputted to the controlling unit 190 via an unillustrated switch, the CPU 191 carries out initial setting process which reads out the controlling program and the controlling data from the ROM and develops them at the RAM.

Figure 18A:
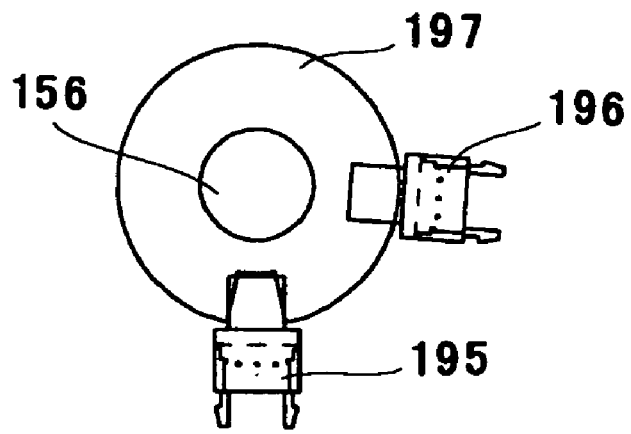
FIG. 18A showing a state of detecting initial positions of a first clamp and a second clamp 7, FIG. 18B showing a state of detecting that the first clamp and the second clamp are located at displaced positions.

Then, as shown in FIG. 18A, the CPU 191 determines as to whether or not the transmission type sensor 195 detected the notch 198 in order to judge whether or not the first clamp 6 and the second clamp 7 are located at the initial positions (positions where the clamps can hold the tubes 8, 9 in the grooves 22, 23, 32, 33 in a parallel state each other. If a negative judgment is made, since the first clamp 6 and the second clamp 7 are not in the initial positions and can not secure regular cutting and connecting operation, the CPU 191 makes the display panel 192 via the display controlling section to display that an unillustrated reset button be pushed. When the unillustrated reset button is pushed, the CPU 191 drives the pulse motor 150 via the actuator controlling section in order to locate the first clamp 6 and the second clamp 7 at the initial positions. If an affirmative judgment is made (or the first clamp 6 and the second clamp 7 are located at the initial positions), the CPU 191 judges whether or not the waste box 142 is full according to a two-level signal from the transmission sensor 143. When an affirmative judgment is made, because the waste box 142 in which the wafers 41 wasted and accommodated is full and it is impossible for the wafer feeding mechanism 170 to feed the wafer 41 from the wafer cassette 120, the CPU 191 makes the display panel 142 to display that the waste box 142 is full and waits until a judgment that the waste box 142 is full is denied according to the signal from the transmission sensor 143. If a negative judgment is made, because it is capable of carrying out regular cutting and connecting operation to the tubes 8, 9, the CPU 191 makes the display panel 192 to display that putting (setting) of tubes 8, 9 is urged and waits until the start button 193 is pushed.

An operator opens the covering body 24 of the first clamp 6 and the covering body 34 of the second clamp 7 to put (set) the tubes 8, 9 into the grooves 22, 23. When the operator opens either one of the covering body 24 of the first clamp 6 or the covering body 34 of the second clamp 7, because the shaft 59 of the first clamp 6 is inserted into the slot 40 of the second clamp 7, another of the covering body 24 of the first clamp 6 or the covering body 34 of the second clamp 7 is linked to open approximately at the same time. (See FIG. 31.) Then, the operator carries out operation for closing the covering body 24 of the first clamp 6 and the covering body 34 of the second clamp 7 to the put tubes 8, 9. (See FIG. 19.) When the operator closes either one of the covering body 24 of the first clamp 6 or the covering body 34 of the second clamp 7, because the shaft 59 of the first clamp 6 is inserted into the slot 40 of the second clamp 7, another of the covering body 24 of the first clamp 6 or the covering body 34 of the second clamp 7 is linked to close approximately at the same time. When the operator further continues to carry out the operation for closing the covering body 24 and the covering body 34, the tip portion 12 of the tube-pushing member 10 firstly abuts and then deforms the tubes 8, 9, which are put in a parallel state at a first position P1 that is an abutting position, to a flat state. (See FIG. 20A.) At this moment, blood inside the tubes 8, 9 at a portion which was pressed by the tube-pushing member 10 is pushed out such that it is excluded in directions of an arrow a and an arrow b in FIG. 20A.

Subsequently, when the operation for closing the covering body 24 and the covering body 34 is carried out further, the pawl member 29 engages the stopping portion 20 of the locking mechanism 26 in the first tube-holding assembly 2, thereby the covering body 24 is locked so as not to open. In this state, the first clamp 6 presses and holds the tubes 8, 9 to a flat state with predetermined pressing force at a second position P2 which is adjacent to the first position P1. At this time, the tube-pushing member 10 disposed so as to contact the first clamp 6 also presses the tubes 8, 9 to an almost squashed state (a state that blood inside the tubes hardly exits) according to the energizing force of the springs 13 in the same manner as the first clamp 6. (See FIG. 20B.)

FIG. 22A shows a state that the covering body 24 of the first clamp 6 is closed to the tubes 8, 9 put in the grooves 22, 23 and a state just before the tip portion 12 of the tube-pushing member 10 presses tubes 8, 9 to a flat state. As shown in FIG. 22B, when the operator continues the operation for closing the covering body 24, the tip portion 12 of the tube-pushing member 12 presses the tubes 8, 9 to a flat state. At this time, pressing operation by the first clamp 6 and the second clamp 7 to the tubes 8, 9 is carried out continuously in a linked manner.

Further, because movement of the second clamp 7 is linked with movement of the first clamp 6, operation for closing the covering body 34 of the second clamp 7 is carried out approximately at the same of the operation for closing the covering body 24 of the first clamp 6. When the pawl member 39 of the locking mechanism 36 in the second clamp 7 engages the stopping portion 30 and the covering body 34 is locked so as not to open, the second clamp 7 which is located so as to contact the tube-pushing member 10, in the same manner as the first clamp 6, presses and holds the tubes 8, 9 to a flat state in an almost squashed state (a state that blood inside the tubes hardly exits) with predetermined pressing force at a third position P3 which is adjacent to the first position P1 and which is a position opposing to the second position P2 via the first position P1. Thus, blood inside the tubes 8, 9 from the second position P2 to the third position P3 via the first position P1, namely, blood inside the tubes 8, 9 at portions being equivalent from a portion pressed by the first clamp 6 to a portion pressed by the second clamp 7 via the tube-pushing member 10 is almost excluded (See FIG. 20B.), pressing and holding operation of the tubes 8, 9 is finished. FIG. 24 shows the first clamp 6, the tube-pushing member 10 and the wafer holder 140 in the finished state, and FIGS. 29A and 30A show a moving state of the cam 158 and the cams 157, 159.

As shown in FIGS. 26A and 27A, in this state, the latch 250 is still held in a state that the tip portion 251 of the latch 250 abuts a side face 210 of the tube-pushing member 10 in an interior of the covering body 24 of the first clamp 6. The rear end portion 252 of the latch 250 is also still held in a state that it advanced to the hole formed at a part of the supporting member 205 disposed downward the first clamp 6 and it has an appropriate interval (gap) to the roller 206.

When an operator pushes the start button 193 of the apparatus 1, the CPU 191 fetches a start signal via the start button controlling section and executes feeding operation for wafer 41 from the wafer cassette 120 according to the wafer feeding mechanism 170.

As stated above, the wafer feeding member 115 which is moved by rotation driving of the pulse motor 110 moves reciprocally between the wafer feeding start position and the wafer feeding end position according to normal and reverse rotation of the pulse motor 110. At this time, the CPU 191 detects a position of the wafer feeding member 115 located between the wafer feeding start position and the wafer feeding end position at a time of normal rotation of the pulse motor 110 with the transmission type sensor 131 one pulse by one pulse in accordance with the revolving amount of the revolving plate 130 which is linked directly with the rotation of the pulse motor 110. Namely, by detecting the piece to be detected 119 of the wafer feeding member 115 which is located at the wafer feeding start position with the transmission type sensor 132, and based on the wafer feeding start position, by detecting the moving amount of the wafer feeding member 115 through the revolving amount of the revolving plate 130 with the transmission type sensor 131, the CPU 191 grasps as to where the wafer feeding member 115 is located.

The CPU 191 judges as to whether or not the wafer feeding member 115 moves more than a predetermined amount (30 mm in this embodiment, See the wafer feeding member 115 shown by a two dotted line in FIG. 28.) from the wafer feeding start position to a direction of the wafer feeding end position. When a negative judgment is made, the CPU 191 continues to grasp the position of the wafer feeding member 115. Incidentally, in this embodiment, the moving amount of the wafer feeding member 115 for feeding the wafer 41 is set to approximately 55 mm.

When an affirmative judgment is made, the CPU 191 judges as to whether or not a difference between a predetermined number of pulses and an actually detected number of pulses, which is not less than predetermined pulses (ex. 20 pulses), occurred, namely, the CPU 191 judges as to whether or not the actually detected number of pulses was less than 20 pulses to the predetermined number of pulses. When an affirmative judgment is made, the CPU 191 determines that feeding malfunction of the wafer 41 occurred and waits until the reset button is pushed. When a negative judgment is made, the CPU 191 determines that normal feeding was made.

When feeding malfunction of the wafer 41 is determined, the CPU 191 stops driving of the pulse motor 110 and makes the display panel 192 to display an error indication (feeding malfunction of wafer) and display that the wafer is to be removed, and drives the pulse motor 150 by a predetermined amount reversely opposing to the normal driving carried out at the time of a series of tube connecting operation to locate the cam 158 at a predetermined position so that the notched portion 178 formed at the cam 158 faces the bearing 172. (See FIG. 29C.) Thus, the bearing 172 is ready to advance into the notched portion 178. In other words, the second clamp 7 is allowed to move to an evacuating position in a direction of an arrow B in FIG. 15 (a direction that allows the second clamp 7 to move in a direction opposite to a direction of the second clamp 7 at the time of connecting the tubes). (In this embodiment, the second clamp is allowed to move by approximately 4 mm.) At this moment, both of the transmission type sensors 195, 196 are in a state that they are shielded by the revolving plate 197. (See FIG. 18C.)

An operator can move the second clamp 7 to the evacuating position and remove the wafer which caused feeding malfunction such as double feeding of the wafers 41 by accessing a space defined between the first clamp 6 and the second clamp 7. (See FIG. 29D.) When the operator pushes an unillustrated reset button after finishing the error cancellation operation, the CPU 191 fetches a signal thereof, then drives the pulse motors 110, 150 to reset various mechanisms to an initial state.

When normal feeding of the wafer 41 is determined, the CPU 191 executes cutting/connecting process. In cutting process, as stated above, the CPU 191 judges as to whether or not the wafer 41 reached the predetermined temperature capable of melting the tubes 8, 9 by judging whether or not the predetermined period of time has lapsed from the time that the wafer 41 was inserted into the wafer holder 140 with an internal clock. When a negative judgment is made, the CPU waits until a predetermined time lapses. When an affirmative judgment is made, the CPU drives the pulse motor 150. This makes the cam 158 and the cams 157, 159 to start rotating in a predetermined direction, yet the cam 158 retains a state shown in FIG. 29A for a predetermined period of time. During this period, the wafer holder 140 swings according to rotation of the cam 159 to ascend a predetermined distance between the first clamp 6 and the second clamp 7. (See FIG. 30B.) Accompanied by this ascending movement, the roller 147 ascends and the supporting member projection portion 54 which abuts the roller 147 also ascends.

Figure 21A:
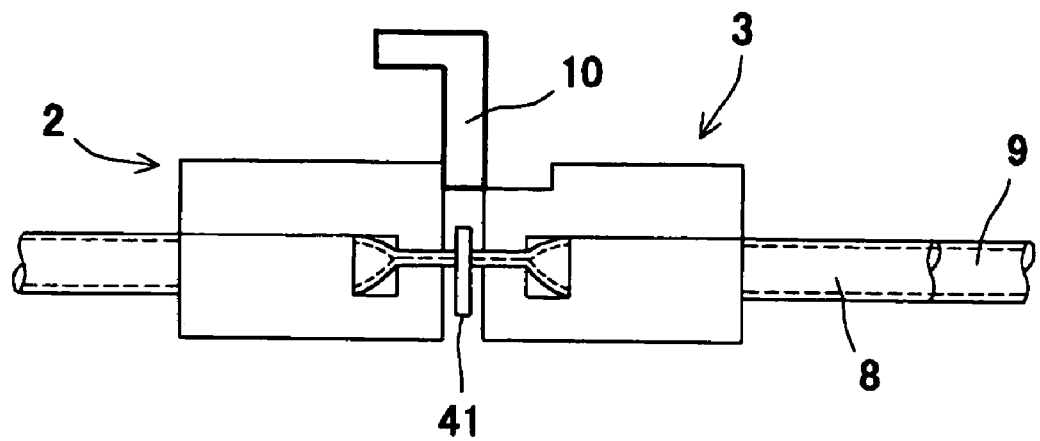
FIG. 21 is a front view illustratively showing operations for the main portions of the tube connecting apparatus, FIG. 21A showing operation 4 thereof, FIG. 21B showing operation 5 thereof and FIG. 21C showing operation 6 thereof.

As shown in FIG. 21A, the projection portion 148 which has the metal roller 147 at its tip and which forms a part of the wafer holder 140 pushes up a part of the tube-pushing member 10 which pressed the tubes 8, 9 at the first position P1, and the heated wafer 41 which is held by the wafer holder 140 advances to the gap between the second position P2 and the third position P3 (between the first clamp 6 and the second clamp 7) to cut the two tubes 8, 9. At this time, the tube-pushing member 10 is brought in a state that it is located at the evacuating position to the wafer 41. (See FIG. 22G.) FIG. 25 shows a state that the wafer holder 140 ascends (swings) and the wafer 41 cuts the tubes 8, 9 set at the predetermined positions. On the other hand, the cam 157 rotates (See FIG.

30B.) from a state shown in FIG. 30A, but the first clamp 6 is kept in a stopped state in the same manner as the second clamp 7 (supporting table 174) shown in FIG. 29A.

At this moment, as shown in FIGS. 26B and 27B, the groove portion 204 of the pushed up tube-pushing member 10 faces the tip portion 251 of the latch 250, and according to the energizing force of the compression spring 209 provided adjacent to a side of the latch 250, the tip portion 251 of the latch 250 advances into the groove portion 204 to latch the tube-pushing member 10 in a stopped (engaged) state at an upper predetermined position. At this time, the rear end portion 252 of the latch 250 is brought in contact with the roller 206 provided at the supporting member 205.

The CPU 191 further continues to drive the pulse motor 150. The wafer holder 140 retains a state shown in FIG. 30B, while the first clamp 6 (supporting member 164) moves by a predetermined distance (8 mm) in a direction of an arrow a of a right side of the FIG. 30C (a direction toward the arrow A in FIG. 15, a direction of the arrow X in FIG. 8) according to rotation of the cam 157. At this moment, the positions of the cut tubes are relatively changed and the portions to be connected face each other. At this time, as shown in FIG. 8, the wafer 41 which has cut the tubes 8, 9 is held at a cutting position thereof in the stopped state. Further at this time, as shown in FIG. 32, the shaft 59 of the first clamp 6 moves inside the slot 40 of the second clamp 7 in a state that the shaft is inserted in the slot 40.

Figure 18B:
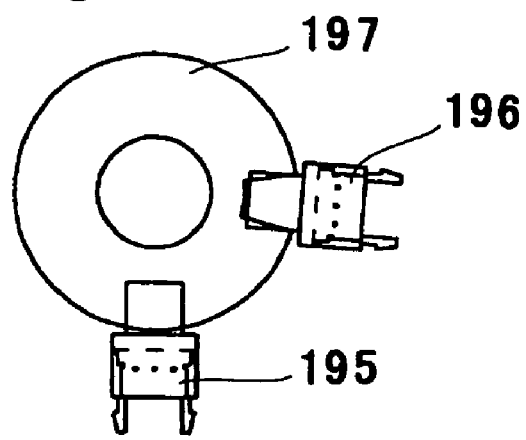
FIG. 18 is a side view showing a revolving plate fitted to a driving shaft and transmission type sensors.
FIG. 18C showing a state of detecting that a bearing is located at a position at which the bearing can advance into a notched portion.
Figure 18C:
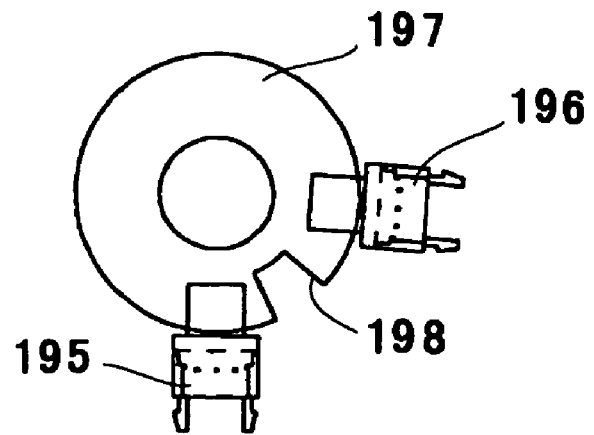
Figure 21B:
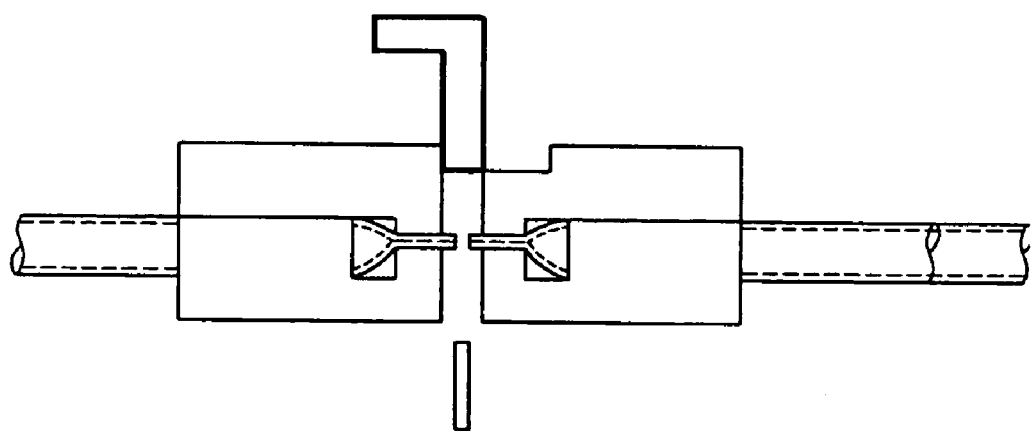
Figure 21C:
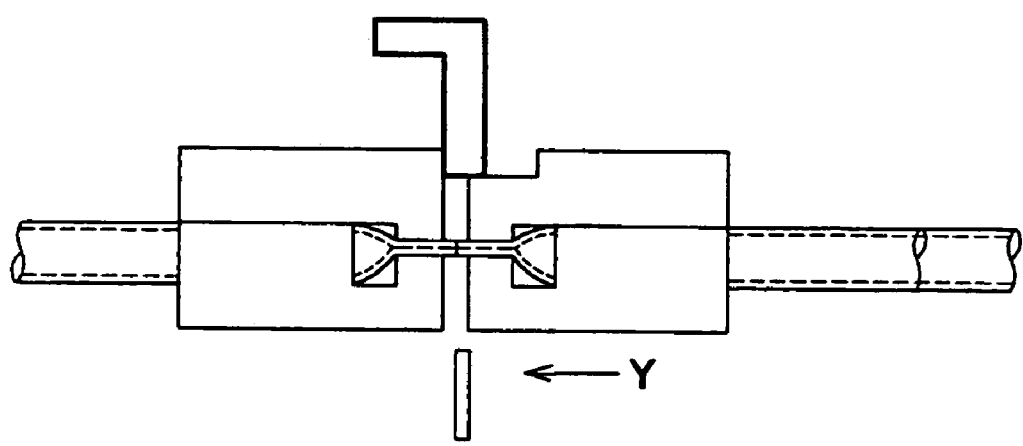

Subsequently, the wafer holder 140 swings to descend (See FIG. 30C.) according to rotation of the cam 159, but the tube-pushing member 10 is held at the above stated evacuating position in a stopped state. (See FIG. 21B.) On the other hand, because the bearing 172 adjacent to the cam 158 slides along a shape of the flange portion 177, the second clamp 7 (the supporting table 174) moves by a predetermined distance (0.6 mm) in a direction of an arrow b in FIG. 29B (a left direction of an arrow B in FIG. 15, a direction of an arrow Y in FIG. 21C). Thus, the connecting operation of the tubes 8, 9 is finished. At this time, as shown in FIG. 18B, the notch 198 is located at a position that faces the transmission type sensor 196, and the CPU 191 confirms a predetermined state (a state that the first clamp 6 is dislocated from the second clamp 7) to stop driving of the pulse motor 150.

The wafer holder 140 descends according to a function of the cam 159 to be located at a predetermined position (a position shown in FIGS. 26A and 27A) when the connecting operation of the tubes is finished, yet the tube-pushing member 10 is held in the stopped state at the upper predetermined position due to the latch 250 (a state shown in FIGS. 26B and 27B).

When an operator lifts the plate piece 28 provided at the tip side of the covering body 24 to cancel the locking mechanism 26 in order to remove the tube(s) that the connecting operation is finished from a main body of the apparatus, the covering body 24 becomes an opened state as shown in FIGS. 26C and 27G. At this time, the covering body 24 and the covering body 34 are in a state that their relative positions are changed or dislocated, however, because the shaft 59 is inserted in the slot 40, when the operator lifts the covering body 24, the covering body 34 is lifted approximately at the same time linked with lifting of the covering body 24. On the other hand, linked with the opening operation of the covering body 24 carried out by the operator, since the roller 206 in a stopped state functions so as to push the inclined face 257 formed at a side (a side of the tube-pushing member 10) of the rear end portion 252 of the latch 250, the inclined face 257 runs away (moves) sequentially due to abutment against the roller 206. This brings the tip portion 251 of the latch 250 to disengage engagement thereof with the groove 204 formed at a part of the tube-pushing member 10 and to release tube-pushing member 10 from the latched (engaged) state at the evacuating position. The released tube-pushing member 10 drops downward to go back to an initial state (See FIGS. 26C and 27C.) In short, linked with the opening operation for the covering body 24, the engaged state of the tube-pushing member 10 at the evacuating position is released (canceled). Incidentally, in a state that the covering body 24 is opened, a space 211 is defined between the covering body 24 and the supporting member 205.

<Effects and the Like>

Next, effects and the like of the tube connecting apparatus 1 in this embodiment will be explained.

In the tube connecting apparatus 1 of this embodiment, in the same manner as the first embodiment, the tube-pushing member 10 whose tip portion 12 is protruded a little more than the pressure closing member 62 of the first clamp 6 is disposed between the first clamp 6 and the second clamp 7, and the tube-pushing member 10 presses the tubes 8, 9 so as to push out the residual blood in the tubes at the pushing portion prior to pressing of the first clamp 6 and the second clamp 7 in order to exclude the blood. Accordingly, the tube connecting apparatus 1 can connect the tubes each other without being influenced by the blood in the tubes at the time of cutting and then connecting the tubes each other. Further, the tube connecting apparatus 1 can realize wet-to-wet connecting between the tubes easily, uniformly and rapidly under a sterilized condition only by putting the tubes 8, 9 in which blood is contained and sealed into the grooves 22, 23, 32 and 33 and locking the covering bodies 24, 34 with the locking mechanisms 26, 36.

Furthermore, in the tube connecting apparatus 1, at the time of connecting the tubes, the positions of the end portions of the cut tubes are changed (shifted) relatively in the state of contacting the wafer 41 such that the end portions to be connected of the tubes face each other, and the end portions to be connected of the tubes are contacted with each other for connecting the tubes at the same time of the descending movement of the wafer 41. In this embodiment, since the structure of the above stated latch 250 is employed and the tube-pushing member 10 is evacuated at the time of moving these parts, smooth cutting operation as well as stable and reliable connecting operation to the tubes 8, 9 can be secured.

Moreover, in the tube connecting apparatus 1 of this embodiment, since the structure for canceling the engaged state of the tube-pushing member 10 at the evacuating position linked with the opening operation of the covering body 24 is employed, the tube-pushing member 10 can be reset to the initial state at a time of starting the next connecting of the tubes carried out by an operator. Accordingly, a series of processing time is shortened and work efficiency can be improved.

Further, in the tube connecting apparatus 1 of this embodiment, the piece to be detected 119 of the wafer feeding member 115 which is located at the wafer feeding start position is detected by the transmission type sensor 132, and from the wafer feeding start position, the moving amount of the wafer feeding member 115 is detected by the revolving plate 130 and the transmission type sensor 131. Accordingly, a feeding amount (feed) of the wafer 41 can be detected precisely. Furthermore, since the feeding malfunction is judged when the actually detected number of pulses is more than the predetermined number of pulses, detection accuracy of the feeding malfunction of the wafer 41 can be improved.

Furthermore, in the tube connecting apparatus 1, since the structure that the bearing 172 is capable of advancing into the notched portion 178 when the feeding malfunction of the wafer 41 caused is employed, an operator can cancel the feeding malfunction of the wafer 41 by moving the second clamp 7 to the evacuating position. Conventionally, when this type of error was occurred, the apparatus was returned to a factory as malfunction of the apparatus to remove the wafer which caused the feeding malfunction through disassembling the apparatus. According to the tube connecting apparatus 1, since an operator can easily carry out error cancellation due to the feeding malfunction of the wafer, requirement of emergency to medical treatment is satisfied, and operability and reliance to the apparatus can be improved.

Further, in the tube connecting apparatus 1, since the wafer feeding mechanism 170 is stopped when the full state of the waste box 142 is detected by the transmission type sensor 143, even if automatic thrusting (feeding) structure for the wafer(s) is employed, the wafer jammed by the following wafer at the conveying path can be prevented. Furthermore, in the tube connecting apparatus 1, whether or not the first clamp 6 and the second clamp 7 can hold the tubes 8, 9 in parallel with each other is judged according to the transmission type sensor 195, and when the clamps are not parallel (not in the initial positions), the apparatus is not started as it is but the apparatus is started after the first clamp 6 and second clamp 7 are returned to the appropriate initial positions according to pushing of the reset button. Accordingly, regular cutting and connecting operation can be always secured.

Moreover, in the tube connecting apparatus 1, since the shaft 59 of the first clamp 6 can be inserted into the slot 40 of the second clamp 7, not only in a state that the first clamp 6 and the second clamp 7 are located at the initial positions (a time of setting the tubes) but also in a state that relative positions thereof are changed (a time of finishing connecting the tubes), when either one of the covering body 24 of the first clamp 6 or the covering body 34 of the second clamp 7 is opened/closed, another of the covering body 24 of the first clamp 6 or the covering body 34 of the second clamp 7 is opened/closed. Accordingly, operability or handling efficiency is improved. Further, in the tube connecting apparatus 1, the cam structure is employed instead of the conventional movement mechanism(s) which moves directly the first clamp 6 and the second clamp 7 in the X, Y directions such as an X, Y table or the like. Accordingly, downsizing of the apparatus per se can be realized.

Incidentally, in this embodiment, an example that the latch 250 and the roller 206 are disposed at a side of the first clamp 6, however, the present invention is not limited to the same. These members may be disposed at a side of the second clamp 7. Further, in this embodiment, an example that the projection portion 148 is formed integrally with the wafer holder 140 was shown, however, the projection portion 148 and the wafer holder 140, each being a separate member, may be fixed so as to be unified. In a case that the projection portion 148 is formed to be slanted like this embodiment, unification (integration) of the separated two members can make a cost for parts lower.

Further, in this embodiment, a structure that the second clamp 7 can move to the evacuating position manually was shown, however, the present invention is not confined to the same. The evacuation movement of the second clamp 7 may be automated by contriving a shape of the cam 158 which regulates the movement of the second clamp or by some other technique. Furthermore, in this embodiment, an example that the tubes 8, 7 are manually put (set) to the clamps 6, 7, however, putting (setting) of the tubes 8, 9 may be automated.

Further, in this embodiment, an example that feeding operation of the wafer 41 from the wafer cassette 120 by the wafer feeding mechanism 170 is started by pushing the start button 193 was exemplified, however, the present invention is not limited to this. The feeding operation may be initiated by pushing the reset button. Furthermore, a structure that a groove is formed at a second pressing unit, more concretely, the slot 40 is formed at the second clamp 7 was shown, however, the present invention is not limited to this. A structure that a dented portion is formed at a bottom of the plate piece 38 of the second clamp may be employed.

Moreover, in this embodiment, a structure that the wafer holder 140 can hold two wafers was exemplified, however, the present invention is not limited to the same. The wafer holder may hold a single wafer, or, three wafers or more.

Further, in the above embodiments (first and second embodiments), an example that connecting of the tubes in which blood is contained and sealed each other was shown, however, the present invention is not restricted to this. The present invention can also realize stable tube connecting in use either in a case of connecting between a tube in which blood is contained and an empty tube or in a case of connecting between empty tubes in which blood is not contained; both have been carried out conventionally.

Furthermore, in the above embodiments, the tube connecting apparatus which connects the two tubes in which blood is contained and sealed was shown. However, the present invention is not restricted to the same. It is also applicable to a tube connecting apparatus which connects three tubes or more, or a tube connecting apparatus which connects tubes in which liquid other than blood is contained and sealed properly each other.

Lastly, in the above embodiments, the saw-shaped pressure closing members 61, 62, 71, 72 and the saw-shaped tube-pushing member 10 were explained. However, since it is sufficient for these members to have a function for pushing out and excluding blood in the tubes 8, 9, they may press and close the tubes 8, 9, for example, at their horizontal faces. Further, the wafer 41 is not limited to the self-heating typed one. For example, the wafer may have a structure heated by a heat source such as an electric heater.

What is claimed is:

1. A tube connecting apparatus having a first holding assembly and a second holding assembly which hold at least two flexible tubes approximately in a parallel state, comprising:
    a first pressing unit which is provided at the first holding assembly and which presses the tubes to a flat state at a second position of the tubes;
    a second pressing unit which is provided at the second holding assembly and which presses the tubes to a flat state at a third position of the tubes;
    a third pressing unit which is disposed between the first and second pressing units and which presses the tubes to a flat state at a first position of the tubes;
    a cutting unit which cuts the tubes at only a single place along the first portion of the tubes; and
    a movement unit which moves at least one of the first and second holding assemblies to change relatively positions of the tubes cut by the cutting unit such that end portions to be connected contact closely each other.

2. A tube connecting apparatus according to claim 1, wherein the third pressing unit is disposed movably to and integrally with either one of the first holding assembly and the second holding assembly.

3. A tube connecting apparatus according to claim 1, wherein the movement unit has a first movement unit which moves the first holding assembly in a first direction which is a width direction of the tubes and a second movement unit which moves the second holding assembly in a second direction which is a length direction of the tubes and which is a direction orthogonal to the first direction.

4. A tube connecting apparatus according to claim 1, wherein the third pressing unit has an energizing section which energizes the tubes to a pressing position at which the tubes are pressed to a flat state and a stopping section which regulates energizing force of the energizing section to stop movement of the third pressing unit.

5. A tube connecting apparatus according to claim 4, wherein the stopping section has a first stopping member for stopping movement of the third pressing unit in a direction of pushing the tubes further from the pressing position and a second stopping member for stopping movement of the third pressing unit to locate the third pressing unit at an evacuating position which is separated from the pressing position so as to allow the cutting unit to cut the tubes.

6. A tube connecting apparatus according to claim 5, wherein the first stopping member comprises a stepped portion which engages the third pressing unit and which is formed at a part of either one of the first and second pressing units which is disposed adjacent to the third pressing unit, and the second stopping member has a lever member for moving the third pressing unit so as to engage and hold the third pressing unit at the evacuating position and an actuator for actuating the lever member movably.

7. A tube connecting apparatus according to claim 6, wherein the cutting unit has a cutting plate for melting and cutting the tubes in a heated state, a cutting-plate holding section for holding the cutting plate and a cutting-plate movement section for moving the cutting-plate holding section, and wherein, when the cutting-plate holding section is moved by the cutting-plate movement section, the third pressing unit is moved to the evacuating position while resisting the energizing force of the energizing section in a state that a first projection member formed at a part of the cutting-plate holding section engages a second projection member formed at a part of the third pressing unit.

8. A tube connecting apparatus according to claim 1, further comprising an evacuation unit which evacuates the third pressing unit to an evacuating position which is separated from a pressing position at which the tubes are pressed to a flat state, and wherein the cutting unit cuts the tubes between the first and second pressing units in a state that the third pressing unit is evacuated to the evacuating position by the evacuation unit.

9. A tube connecting apparatus according to claim 8, wherein the movement unit has a first movement unit which moves the first holding assembly in a first direction which is a width direction of the tubes and a second movement unit which moves the second holding assembly in a second direction which is a length direction of the tubes and which is a direction orthogonal to the first direction, wherein the first movement unit moves the first holding assembly in the first direction to change relatively positions of the tubes cut by the cutting unit such that end portions of the tubes to be connected face each other and the second movement unit moves the second holding assembly in the second direction such that the end portions of the tubes to be connected contact closely each other, and wherein a distance between the first pressing unit provided at the first holding assembly which is movable in the first direction and the cutting unit is set to be larger than a distance between the second pressing unit provided at the second holding assembly which is movable in the second direction and the cutting unit.

10. A tube connecting apparatus according to claim 9, wherein a moving distance of the first holding assembly in the first direction is set to be larger than a moving distance of the second holding assembly in the second direction.

11. A tube connecting apparatus according to claim 1, wherein the first pressing unit has a first pressing section for pressing the tubes to a flat state and a first supporting section for supporting the tubes which are pressed by the first pressing section, the second pressing unit has a second pressing section for pressing the tubes to a flat state and a second supporting section for supporting the tubes which are pressed by the second pressing section, and further comprising:

an evacuation guiding unit which guides the third pressing unit in a direction of an evacuating position when the cutting unit cuts the tubes; and a stopping unit which is provided at the first or second pressing unit and which stops the third pressing unit to locate the third pressing unit at the evacuating position.

12. A tube connecting apparatus according to claim 11, further comprising an energizing unit which is disposed adjacent to the stopping unit and which energizes the stopping unit in a direction of the third pressing unit.

13. A tube connecting apparatus according to claim 11, wherein a groove portion is formed at a part of the third pressing unit, and wherein, when the third pressing unit is guided to the evacuating position by the evacuation guiding unit, the stopping unit engages the groove portion to stop the third pressing unit at the evacuating position.

14. A tube connecting apparatus according to claim 11, wherein the cutting unit has a cutting plate for melting and cutting the tubes in a heated state, a cutting-plate holding section for holding the cutting plate and a cutting-plate movement section for moving the cutting-plate holding section, and wherein the evacuation guiding unit is connected or integrally formed with the cutting-plate holding section.

15. A tube connecting apparatus according to claim 11, further comprising a cancellation unit which is provided at the first or second supporting section and which cancels a stopping state of the third pressing unit according to the stopping unit.

16. A tube connecting apparatus according to claim 15, wherein the cancellation unit cancels the stopping state of the third pressing unit according to the stopping unit linking with separating movement of the first or second pressing unit from a side of the first or second supporting section.

17. A tube connecting apparatus according to claim 16, wherein the stopping unit has an inclined face at a part thereof and the cancellation unit has a rotatable roller member, and wherein the stopping state of the third pressing unit is canceled in a manner that the stopping unit leaves the groove portion of the third pressing unit due to that the stopping unit is pushed along the inclined face by the roller member.

18. A tube connecting apparatus according to claim 11, wherein one of the first or second pressing unit has a projection portion projecting toward another of the first or second pressing unit and the another of the first or second pressing unit has a groove portion or a dented portion into which the projection portion is inserted, and wherein the groove portion or the dented portion has a shape which allows the projection portion to move when the first or second holding assembly is moved by the movement unit.

19. A tube connecting method for cutting and then connecting at least two flexible tubes, comprising:

pressing the tubes put approximately in a parallel state at a first position to deform the tubes to a flat state;

pressing the tubes at a second position adjacent to the first position to hold the tubes in a flat state;

pressing the tubes at a third position which is adjacent to the first position and which is a position opposing to the second position via the first position to hold the tubes in a flat state;

advancing a heated cutting plate between the second and third positions to cut the tubes;

moving relatively the tubes which have been cut to face end portions of the tubes to be connected each other; and evacuating the cutting plate from a predetermined cutting position located between the second and third positions to contact the end portions of the tubes closely each other for connecting the tubes, wherein, the cutting of the tubes comprises advancing the cutting plate to the cutting position in correspondence with cancelling the pressing of the tubes at the first position.

20. A tube connecting method according to claim 19 wherein, when the tubes which have been cut are moved relatively, the tubes are moved along at least one face side of the cutting plate while the cutting plate is kept located at the cutting position.

* * * * *

UNITED STATES PATENT AND TRADEMARK OFFICE
CERTIFICATE OF CORRECTION

PATENT NO. : 7,657,996 B2  Page 1 of 1
APPLICATION NO. : 10/525972
DATED : February 9, 2010
INVENTOR(S) : Sano et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1155 days.

Signed and Sealed this

Thirtieth Day of November, 2010

David J. Kappos
*Director of the United States Patent and Trademark Office*